(12) United States Patent
Buehlmayer et al.

(10) Patent No.: US 7,612,238 B2
(45) Date of Patent: Nov. 3, 2009

(54) AMINO-PROPANOL DERIVATIVES

(75) Inventors: Peter Buehlmayer, Arlesheim (CH); Klaus Hinterding, Wittlingen (DE); Carsten Spanka, Rheinfelden (DE); Frédéric Zecri, Bartenheim (FR)

(73) Assignee: Novartis AG, Basel (CH)

( * ) Notice: Subject to any disclaimer, the term of this patent is extended or adjusted under 35 U.S.C. 154(b) by 4 days.

(21) Appl. No.: 10/526,760

(22) PCT Filed: Sep. 12, 2003

(86) PCT No.: PCT/EP03/10175

§ 371 (c)(1), (2), (4) Date: Mar. 4, 2005

(87) PCT Pub. No.: WO2004/024673

PCT Pub. Date: Mar. 25, 2004

(65) Prior Publication Data

US 2006/0166940 A1    Jul. 27, 2006

(30) Foreign Application Priority Data

Sep. 13, 2002  (GB) ................... 0221313.0
Sep. 30, 2002  (GB) ................... 0222617.3

(51) Int. Cl.
C07C 211/27  (2006.01)
C07F 9/09    (2006.01)
A61K 31/135  (2006.01)

(52) U.S. Cl. ................ 564/355; 558/166; 514/114; 514/653

(58) Field of Classification Search ............... None
See application file for complete search history.

(56) References Cited

U.S. PATENT DOCUMENTS 5,604,229 A    2/1997  Fujita et al.

6,437,165 B1   8/2002  Mandala et al.

FOREIGN PATENT DOCUMENTS

| EP | 0 627 406 | 12/1994 |
|----|-----------|---------|
| EP | 0 778 263 | 6/1997  |
| EP | 1 002 792 | 5/2000  |
| WO | WO 02/18395 | 3/2002 |
| WO | WO 02/076995 | 10/2002 |

OTHER PUBLICATIONS

Database CAPLUS on STN, Acc. No. 1939:32109, Butler et al., Journal of the American Chemical Society (1939), 61, p. 914-915 (abstract).*
Database CAPLUS on STN, Acc. No. 1993:560817, Boesten et al., EP 534553 (Mar. 31, 1993) (abstract).*
Database CAPLUS on STN, Acc. No. 1995:494381, Fujita et al., WO 9408943 (Apr. 28, 1994) (abstract).*
Database CALUS on STN, Acc. No. 1996:336460, Fujita et al., W09606068 (Feb. 29, 1996) (abstract).*
Adachi et al., "Design, Synthesis, and Structure-Activity Relationships of 2-Substituted-2-Amino-1,3-Propanediols: Discovery of a Novel Immunosuppressant, FTY720", Bioorganic & Medicinal Chemistry Letters, vol. 5, No. 8, pp. 853,856 (1995).

* cited by examiner

*Primary Examiner*—Brian J Davis
(74) *Attorney, Agent, or Firm*—Hoxie & Associates, LLC

(57) ABSTRACT

Compounds of formula I

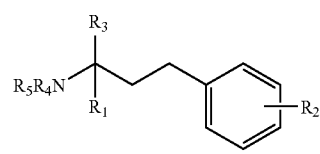

wherein $R_1$, $R_2$, $R_3$, $R_4$ and $R_5$ are as defined in the specification, processes for their production, their uses and pharmaceutical compositions containing them.

6 Claims, No Drawings

AMINO-PROPANOL DERIVATIVES

The present invention relates to amino-propanol derivatives, process for their production, their uses and pharmaceutical compositions containing them.

More particularly, the invention provides a compound of formula I

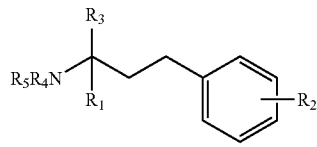

wherein
$R_1$ is $C_{1-6}$alkyl optionally substituted by OH, $C_{1-2}$alkoxy or 1 to 6 fluorine atoms; $C_{2-6}$alkenyl; or $C_{2-6}$alkynyl;

$R_2$ is $R_2'$ or $R_2''$
wherein $R_2'$ is $X_1$, —O—$X_1$, —CO—$X_1$, —CH(OH)—$X_1$, —C(NOR$_6$)—$X_1$, —S—$X_1$, —SO—$X_1$, —SO$_2$—$X_1$ or —N(C$_{1-6}$alkyl)—$X_1$ wherein $X_1$ is $C_{3-8}$ alkyl substituted by 1 to 17 fluorine atoms and optionally interrupted in the carbon chain by one or more O, C=O, CH—OH or C=NOR$_6$ and/or one carbon-carbon double or triple bond; pentyl substituted by $C_{1-3}$alkyl and optionally interrupted in the carbon chain by one or more O, C=O, CH—OH or C=NOR$_6$ and/or one carbon-carbon double or triple bond; $C_{2-8}$alkyl-$C_{3-6}$cycloalkyl wherein the $C_{2-8}$alkyl moiety is optionally interrupted in the carbon chain by one or more O, C=O, CH—OH or C=NOR$_6$ and/or one carbon-carbon double or triple bond, and the $C_{3-6}$cycloalkyl and/or the $C_{2-8}$alkyl is substituted by 1 to 17 fluorine atoms; and each of $R_6$, independently, is H, $C_{1-4}$alkyl, $C_{2-4}$alkenyl, $C_{2-4}$alkynyl or benzyl; and and wherein $R_2''$ is X—CH$_2$—CH$_2$—R attached in position para, wherein X is O; CH$_2$; or C=O; and R is a residue of formula (b)

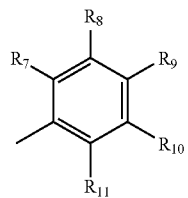

wherein each of $R_7$ to $R_{11}$, independently, is H; halogen; CN; CF$_3$; OCF$_3$; OCHF$_2$; $C_{1-6}$alkyl; $C_{1-6}$alkoxy; $C_{3-6}$cycloalkyl; $C_{3-6}$cycloalkoxy; acyl; or optionally substituted phenyl; or $R_9$ and $R_{10}$ form together 3,4-[—O(CH$_2$)$_r$O—] wherein r is 1 or 2; or ($R_7$ and $R_8$) or ($R_8$ and $R_9$) together with the carbon atoms to which they are attached, form a fused cyclic or heterocyclic ring and the remaining $R_9$ to $R_{11}$ or $R_7$ and $R_{10}$ and $R_{11}$, respectively, are as defined above; or R is α- or β-naphthyl optionally substituted by one to 5 substituents as defined above for $R_7$ to $R_{11}$;

$R_3$ is Z-$X_2$ wherein Z is CH$_2$, CHF or CF$_2$ or CHMe and $X_2$ is OH or a residue of formula (a)

wherein $Z_1$ is a direct bond, CH$_2$, CHF, CF$_2$ or O, and each of $R_{12}$ and $R_{13}$,
independently, is H or $C_{1-4}$alkyl optionally substituted by 1, 2 or 3 halogen atoms; and
each of $R_4$ and $R_5$, independently, is H, $C_{1-4}$alkyl optionally substituted by 1, 2 or 3 halogen atoms, or acyl in free form or in salt form.

Alkyl or alkyl moiety may be straight or branched chain, e.g. methyl, ethyl, propyl, iso-propyl or butyl. Alkenyl may be e.g. vinyl. Alkynyl may be e.g. propyn-2-yl. Cycloalkyl may be e.g. $C_{3-6}$cycloalkyl.

Acyl may be a residue W—CO wherein W is $C_{1-6}$alkyl, $C_{3-6}$cycloalkyl, phenyl or phenyl$C_{1-4}$alkyl. When the phenyl as $R_7$, $R_8$, $R_9$, $R_{10}$, or $R_{11}$ is substituted, it may be substituted by one to five substituents as defined above for $R_7$ to $R_{11}$, except phenyl.

Examples of saturated or unsaturated heterocyclic rings formed by ($R_7$ and $R_8$) or ($R_8$ and $R_9$) together with the carbon atoms to which they are attached include e.g. rings containing 1 or 2 heteroatoms selected from N, O or S, e.g. thienyl, furyl, pyrrolyl, oxazolyl, isoxazolyl, imidazolyl, thiazolyl, isothiazolyl, pyrazolyl, dehydrodioxolane or dehydrodioxane. Examples of cyclic rings formed by ($R_7$ and $R_8$) or ($R_8$ and $R_9$) together with the carbon atoms to which they are attached include e.g. cyclopentene, cyclohexene.

Halogen may be F, Cl or Br, preferably F or Cl.

Preferably, the alkyl group or moiety in $R_2'$ contains at least 2 fluorine atoms, more preferably at least 3, particularly from 3 to 8 fluorine carbon atoms. The fluorine atoms preferably replace 1, 2 or 3 hydrogen atoms present on the terminal carbon atoms of the alkyl group or moiety in $R_2$, i.e. at the ending remote from the phenyl group. By terminal carbon atoms is meant the last, and/or the penultimate, and/or the antepenultimate, etc. up to the last 8 carbon atoms.

When the cycloalkyl moiety in $R_2'$ is substituted by F, from one up to all hydrogen atoms present in the cycloalkyl moiety may be substituted by F.

$R_2'$ is preferably in position para.

Preferably $R_2'$ is $X_1$, —O—$X_1$, —CO—$X_1$, —CH(OH)—$X_1$ or —C(NOR$_6$)—$X_1$, more preferably $X_1$, —COX$_1$ or —O—$X_1$.

When $R_2'$ does not comprise a cycloalkyl moiety, it is preferably a residue of formula (c)

wherein
Y is a direct bond, O, CO, CHOH or C=NOR$_6$ wherein $R_6$ is as defined above;
n is 0, 1, 2, 3, 4 or 5;
m is 0, 1, 2, 3, 4, 5 or 6, provided that the sum of n+m is 3-8
each of p and q, independently, is 0, 1, 2 or 3, the chain (CH$_2$)$_n$—(CF$_2$)$_m$—CH$_p$F$_q$ being optionally interrupted by one carbon-carbon double or triple bond, one CO or one or two oxygen atoms.

More preferably, $R_2'$ has one of the following significances:
—Y—C$_n$F$_{2n+1}$ wherein n=3-8 and Y is CH$_2$, O or C=O;

—Y—CH$_2$C$_n$F$_{n+1}$ wherein n=1-7 and Y is CH$_2$, O or C=O;
—Y—CH$_2$CH$_2$C$_n$F$_{2n+1}$ wherein n=1-6 and Y is CH$_2$, O or C=O;
—Y—CH$_2$CH$_2$CH$_2$ C$_n$F$_{2n+1}$ wherein n=1-5 and Y is CH$_2$, O or C=O;
—Y—(CH$_2$)$_n$F wherein n=1-7 and Y is CH$_2$, O or C=O;
—Y—(CH$_2$)$_n$CF$_3$ wherein n=1-6 and Y is CH$_2$, O or C=O;
—Y—(CH$_2$)$_n$CF$_2$CH$_3$ wherein n=1-4 and Y is CH$_2$, O or C=O;
—Y—(CH$_2$)$_n$(CF$_2$)$_m$CHF$_2$ wherein n=0-3, m=1-6, n+m=3-7 and Y is CH$_2$, O or C=O; or
—Y—(CH$_2$)$_n$C(O)CF$_3$ wherein n=1-5 and Y is CH$_2$, O or C=O.

Further preferred significances for R$_2$' are e.g.

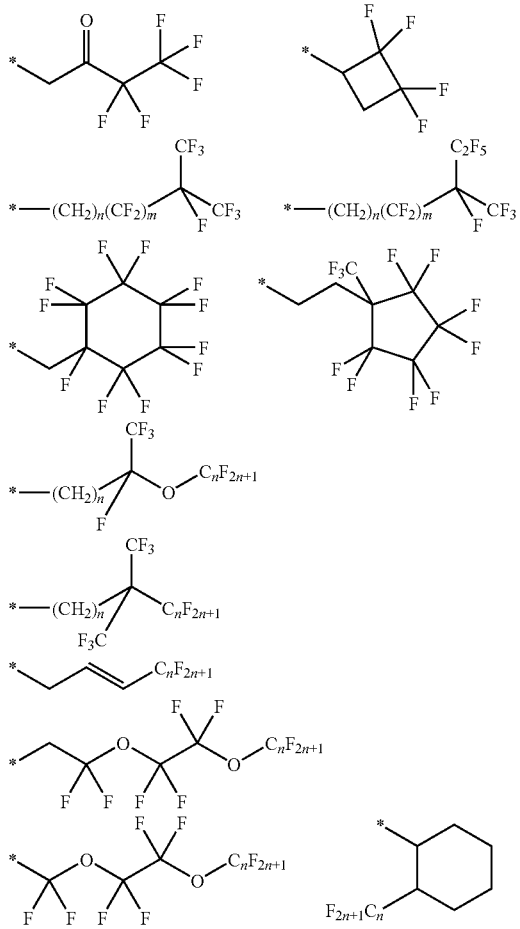

wherein n and m have one of the significances given above, the sum n+m being 3-8, and the asterisk * means the attachment to the phenyl ring directly or through O, CO, CHOH, C(NOR$_6$), S, SO, SO$_2$ or N(C$_{1-6}$alkyl). Preferably the attachment of R$_2$' to the phenyl ring is through O.

Further examples of preferred significances for R$_2$' are e.g.

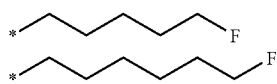

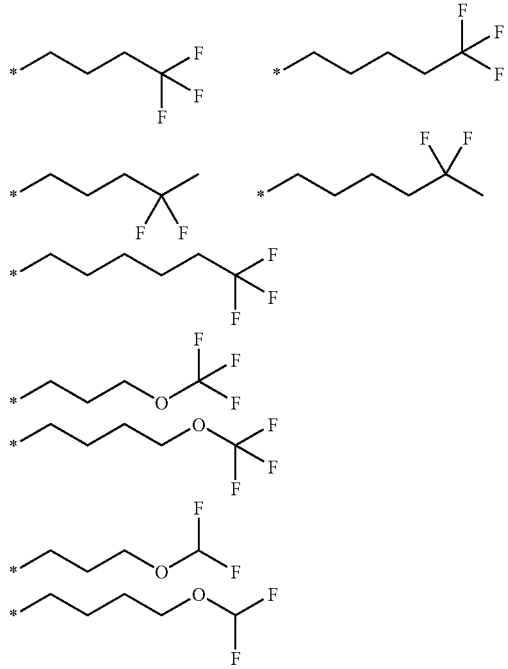

wherein the asterisk * is as defined above.

Most preferably R$_2$' is —O(CH$_2$)$_3$CF$_2$CF$_3$, —O(CH$_2$)$_4$CF$_2$CF$_3$, —O(CH$_2$)$_2$CF$_2$CF$_3$, —(CH$_2$)$_4$C$_2$F$_5$, —(CH$_2$)$_5$C$_2$F$_5$, —(CH$_2$)$_3$C$_2$F$_5$, —C(O)(CH$_2$)$_3$CF$_2$CF$_3$, —C(O)(CH$_2$)$_4$CF$_2$CF$_3$ or —C(O)(CH$_2$)$_2$CF$_2$CF$_3$, preferably in position para.

Preferably, R$_2$" is X—CH$_2$—CH$_2$—R attached in position para, wherein R is β-naphthyl optionally substituted by one to 5 substituents as defined for R$_7$ to R$_{11}$, or wherein R is a residue of formula (b), wherein
  each of R$_7$ to R$_{11}$, independently, is Cl, Br, F, CF$_3$, OCF$_3$, C$_{1-6}$alkyl, C$_{1-6}$alkoxy, or optionally substituted phenyl, and/or
  one or two of the residues R$_7$ to R$_{11}$ are not H, and the other residues R$_7$ to R$_{11}$ are H.
Preferably Z$_1$ is O.
Preferably Z is CH$_2$.
Preferably X$_2$ is OH or OPO$_3$H$_2$.
Preferably R$_1$ is methyl; ethyl or C$_{1-5}$s alkyl substituted by OH.

Compounds of formula I may exist in free form or in salt form, e.g. addition salts with e.g. inorganic acids, such as hydrochloride, hydrobromide or sulfate, salts with organic acids, such as acetate, fumarate, maleate, benzoate, citrate, malate, methanesulfonate or benzenesulfonate salts; when R$_7$ or R$_8$ is H, the phosphate group may also be present in salt form, e.g. an ammonium salt or salts with metals such as sodium, potassium, calcium, zinc or magnesium, or a mixture thereof. Compounds of formula I and their salts, in hydrate or solvate form are also part of the invention.

When the compounds of formula I have asymetric centers in the molecule, various optical isomers are obtained. The present invention also encompasses enantiomers, racemates, diastereoisomers and mixtures thereof. For example, the central carbon atom bearing R$_1$, R$_3$ and NR$_4$R$_5$ may have the R or S configuration. Compounds having the following 3-dimensional configuration are generally preferred:

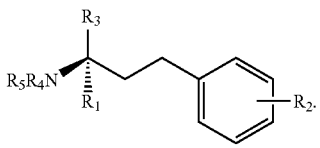

Moreover, when the compounds of formula I include geometric isomers, the present invention embraces cis-compounds, trans-compounds and mixtures thereof. Similar considerations apply in relation to starting materials exhibiting asymmetric carbon atoms or unsaturated bonds as mentioned above, e.g. compounds of formula II, III or IV as indicated below.

The present invention also includes a process for the preparation of a compound of formula I which process comprises
a) for a compound of formula I wherein $R_3$ is $Z\text{-}X_2$, $X_2$ being OH, removing the protecting group present in a compound of formula II

II

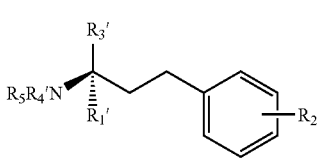

wherein $R_1$, $R_2$ and $R_5$ are as defined above, $R'_3$ is $Z\text{-}X_2$ wherein $X_2$ is OH and $R'_4$ is an amino protecting group, or
b) for a compound of formula I wherein $R_3$ is $Z\text{-}X_2$, $X_2$ being a residue of formula (a), removing the protecting groups present in a compound of formula III

III

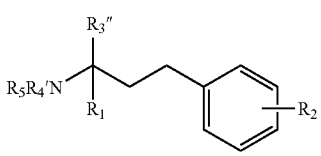

wherein $R_1$, $R_2$, $R'_4$ and $R_5$ are as defined above, and $R''_3$ is $Z\text{-}X_2$ wherein $Z$ is as defined above and $X_2$ is a residue of formula (a')

(a')

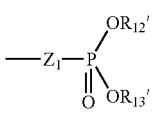

wherein $Z_1$ is as defined above and each of $R'_{12}$ or $R'_{13}$ is a hydrolysable or hydrogenolysable group or $R'_{12}$ and $R'_{13}$ form together a divalent bridging residue optionally fused to a ring (e.g. benzene ring), and, where required, converting the compounds of formula I obtained in free form into the desired salt form, or vice versa.

Process step a) may be carried out in accordance with methods known in the art. The removal of the amino protecting groups may conveniently be performed according to methods known in the art, e.g. by hydrolysis, e.g. in an acidic medium, for example using hydrochloric acid. Examples of protecting groups for amino groups are e.g. as disclosed in "Protective Groups in Organic Synthesis" T. W. Greene, J. Wiley & Sons NY, $2^{nd}$ ed., chapter 7, 1991, and references therein, e.g. benzyl, p-methoxybenzyl, methoxymethyl, tetrahydropyranyl, trialkylsilyl, acyl, tert.-butoxy-carbonyl, benzyloxycarbonyl, 9-fluorenyl methoxy carbonyl, trifluoroacetyl, and the like.

In the residue of formula (a'), each of $R'_7$ and $R'_8$ may have the significance of e.g. phenyl or benzyl or form together a cyclic system such as in 1,5-dihydro-2,4,3-benzodioxaphosphepin.

Process step (b) may be performed according to methods known in the art, e.g. by hydrolysis, e.g. in a basic medium when $R'_7$ and $R'_8$ are each a hydrolysable group, for example using a hydroxide such as barium hydroxide. It may also be performed by hydrogenolysis, e.g. in the presence of a catalyst, e.g. Pd/C, followed by hydrolysis, e.g. in an acidic medium, e.g. HCl, or by acid treatment, e.g. using HCl, e.g. if both $R_{12}$ and $R_{13}$ are tert-butyl. Compounds of formulae II and III, used as starting materials, and salts thereof are also novel and form part of the invention.

The present invention also includes a process for the preparation of a compound of formula II, wherein $R_2$ is $R_2'$ which is $-O-X_1$ or $R_2$ is $R_2''$ which is $-O-CH_2-CH_2-R$, which process comprises alkylating a compound of formula IV

IV

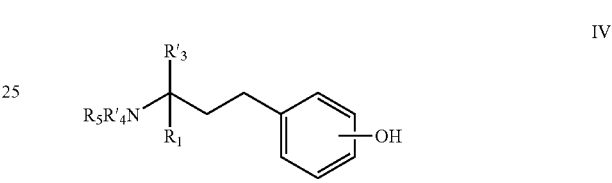

wherein $R_1$, $R_3'$, $R_4'$ and $R_5$ are as defined above, to introduce the desired residue $X_1$ or $-CH_2-CH_2-R$.

Alkylation of the compounds of formula IV may be performed according to methods known in the art, e.g. by nucleophilic substitution, e.g. by reaction with an alkylating agent $X_1-X_3$ or $R-CH_2-CH_2-X$ wherein R is as defined above and $X_3$ is mesylate, tosylate, triflate, nosylate or an halogen, e.g. chloride, bromide or iodide. The alkylation may also be carried out by following the Mitsunobu protocol (e.g. as disclosed in Hughes, Organic Preparations and Procedures International 28, 127-64, 1996 or D. L. Hughes, Org. React. 42, 335, 1992), in solution or on solid phase support synthesis, e.g. by attaching the compound of formula IV to a resin. Alternatively, either triphenylphosphine or e.g. diethyl azocarboxylate bound to a resin, e.g. polystyrene, can be used.

Compounds of formula III wherein $R'_{12}$ and $R'_{13}$ form a cyclic system, may be prepared as follows:

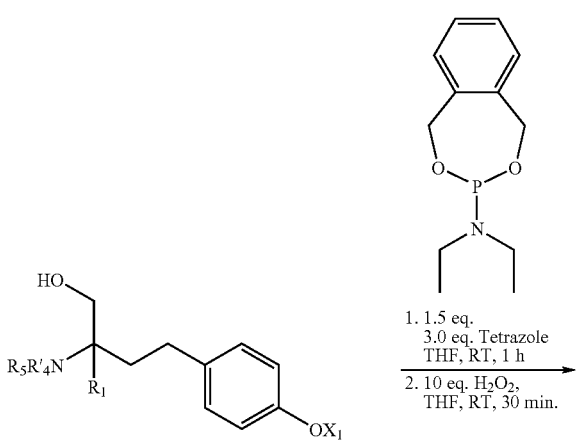

1. 1.5 eq.
   3.0 eq. Tetrazole
   THF, RT, 1 h
2. 10 eq. $H_2O_2$,
   THF, RT, 30 min.

-continued

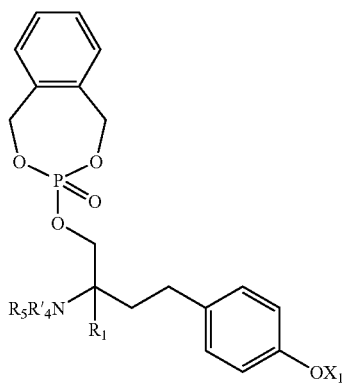

wherein $X_1$, $R'_1$, $R'_4$ and $R_5$ are as defined above.

Insofar as the production of the starting materials is not particularly described, the compounds are known or may be prepared analogously to methods known in the art or as disclosed in the Examples hereinafter.

The following Examples are Illustrative of the Invention. Melting points are uncorrected.

RT=room temperature
DCM=dichloromethane
Bn=benzyl
THF=tetrahydrofuran
DMF=dimethylformamide
DMSO=dimethylsulfoxide
MTBE=methyl tert.-butyl ether
AcOEt=ethyl acetate
DEAD=Diethyl azodicarboxylate
DBAD=di tert.-butyl azidodicarboxylate
Ts=Tosylate
Ms=Mesylate

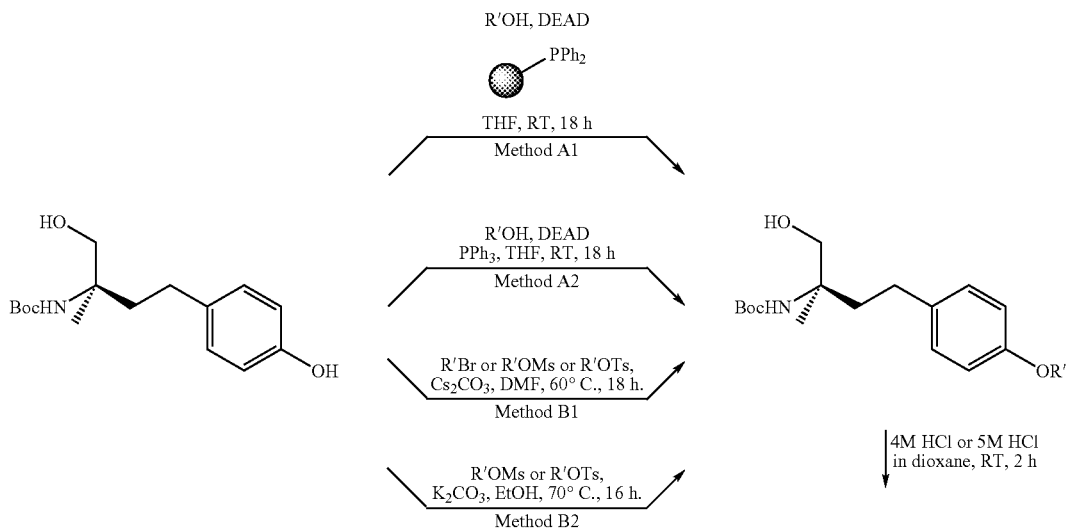

Scheme 1:
Preparation of aminopropanols $R' = $ —$X_1$ or —$CH_2$—$CH_2$—R wherein $X_1$ and R are as defined above Scheme 2:
Preparation of phosphates of aminopropanols
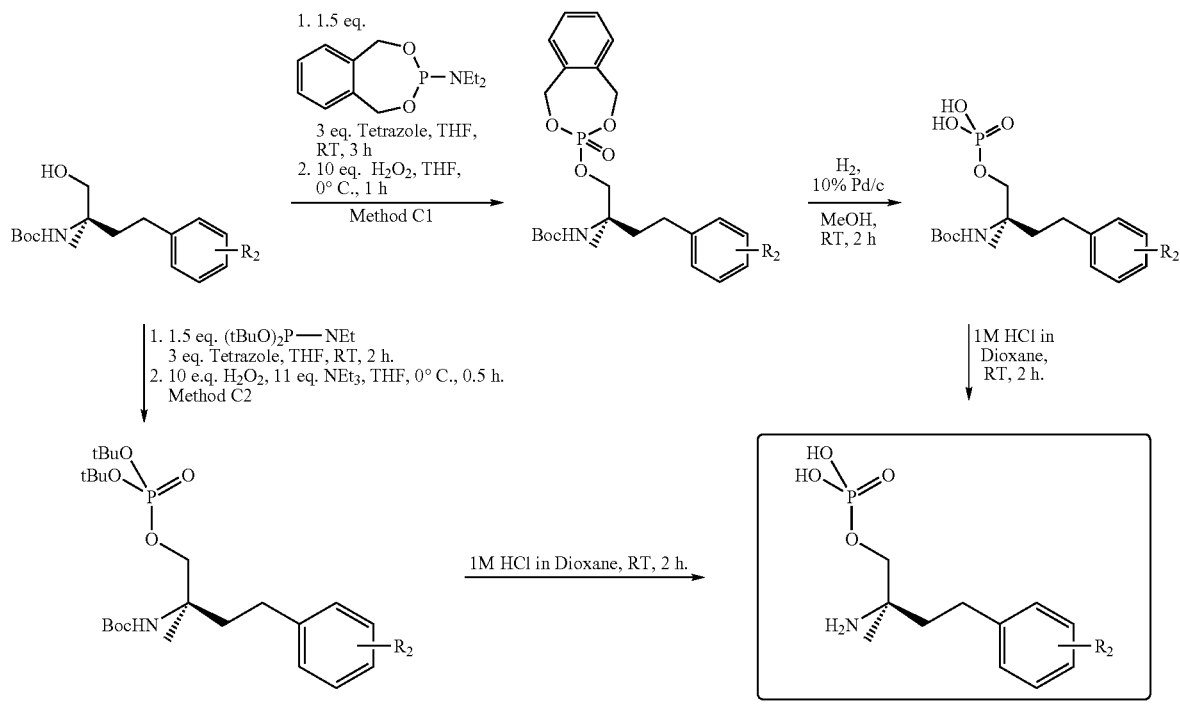
Scheme 3:
Preparation of amino propane-1,3-diols and of corresponding phosphates
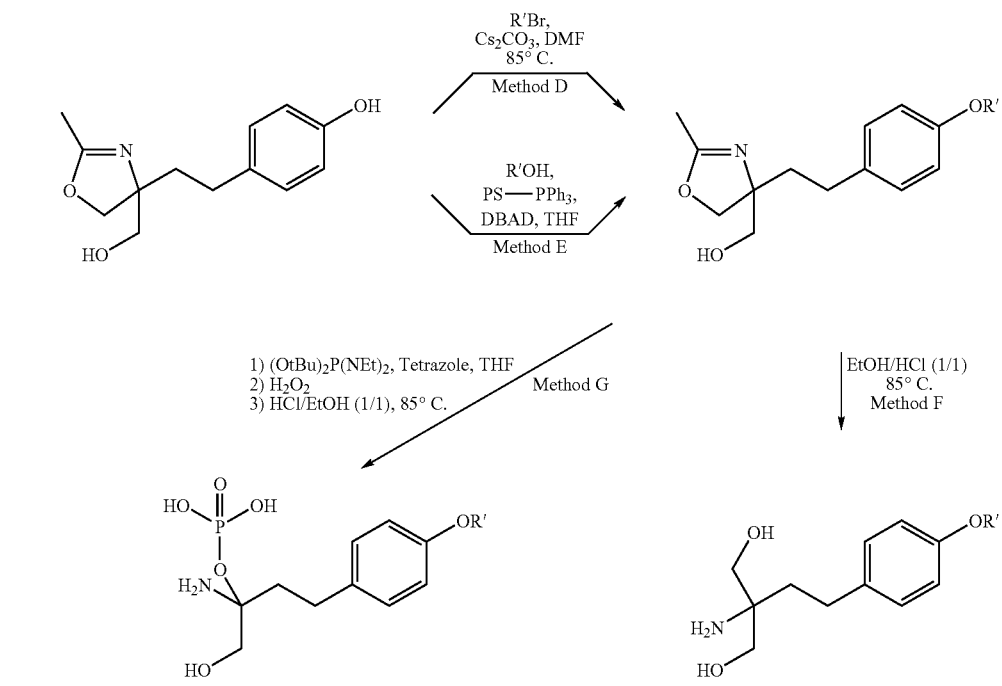
R' = —X₁ or —CH₂—CH₂—R
wherein X₁ and R are as defined above

EXAMPLE 1

(R)-2-Amino-2-methyl-4-[4-(4,4,5,5,5-pentafluoro-pentyloxy)-phenyl]-butan-1-ol Hydrochloride

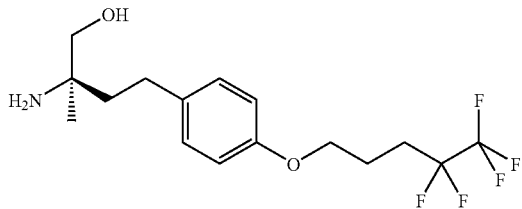

To tert-butyl {(R)-1-hydroxy-2-methyl-4-[4-(4,4,5,5,5-pentafluoro-pentyloxy)-phenyl]-but-2-yl}-carbamate (25 mg, 0.055 mmol) is added 4 M HCl in dry dioxane (1 ml). The clear colorless solution is stirred for 2 h protected from moisture. Then, the solution is evaporated to dryness and the partially crystalline residue is taken up in dry ether (5 ml). Sonication for 10 min gives a precipitate of colorless crystals. The product is filtered off, washed with cold ether (3×1 ml), and dried in vacuo to afford the title compound in form of a non hygroscopic colorless microcrystalline powder: mp. 186-189° C. MS (ESI+): 356 (MH+), ¹H-NMR (400 MHz, CD$_3$OD): δ 1.35 (s, 3H, 2-Me), 1.91 (cm, 2H, 3-CH$_2$), 2.06 (cm, 2H, 2'-CH$_2$), 2.35 (cm, 2H, 3'-CH$_2$), 2.63 (cm, 2H, 4-ArCH$_2$), 3.55 (d, 1H, $^2J$=12.1, 1-CH$_\alpha$), 3.63 (d, 1H, $^2J$=11.9, 1-CH$_\beta$), 4.06 (t, 3H, $^3J$=7.1, 1'-OCH$_2$), 6.88 ('d', 2H, J=11.0, ArH), 7.18 ('d', J=10.8 Hz, ArH).

The required starting material may be prepared according to following procedure:

a) tert-Butyl {(R)-1-hydroxy-2-methyl-4-[4-(4,4,5,5,5-pentafluoro-pentyloxy)-phenyl]-but-2-yl}-carbamate General Procedure Method A1 (Mitsunobu Reaction Using Polystyrene-Triphenyl Phosphine; Scheme 1)

To a solution of tert-butyl [(R)-1-hydroxy-4-(4-hydroxy-phenyl)-2-methyl-but-2-yl]-carbamate (100 mg, 0.34 mmol) and 4,4,5,5,5-pentafluoropentan-1-ol (50 μl, 0.37 mmol, 1.1 eq.) in dry THF (5 ml) is added triphenylphosphine-polystyrene 1.10 mmol g$^{-1}$ (370 mg, 0.41 mmol, 1.2 eq.). The suspension is shaken for 15 min to allow the resin to swell. Then, diethyl azodicarboxylate (67 μl, 0.41 mmol, 1.2 eq.) is injected in one portion. The suspension obtained is shaken under argon at RT overnight. Then, the polymer is filtered off and washed with THF (3×2 ml). Evaporation of the combined filtrates affords a yellow semi-crystalline residue. Purification by flash chromatography (FlashMaster II, MTBE/hexanes gradient: 0% MTBE->30% MTBE within 30 min.; 30% MTBE->60% MTBE within 10 min) gives colorless crystals: mp. 90-92° C., MS (ESI+): 456 (MH+), 400 (MH+-tBu), 356 (MH+-Boc), ¹H-NMR (400 MHz, CDCl$_3$): δ 1.16 (s, 3H, 2-Me), 1.37 (s, 9H, tBu), 1.79 (cm, 1H, 3-CH$_\alpha$), 1.91-2.04 (m, 3H, 3-CH$_\alpha$+2'-CH$_2$), 2.12-2.28 (m, 2H, 3'-CH$_2$), 2.51 (cm, 2H, 4-CH$_2$Ar), 3.58 (d, 1H, $^2J$=10.9, 1-CH$_\alpha$), 3.63 (d, 1H, $^2J$=11.2, 1-CH$_\beta$), 3.94 (t, 3H, $^3J$=7.3, 1'-ArOCH$_2$), 6.75 ('d', 2H, J=10.2, ArH), 7.05 ('d', J=10.5, ArH).

General Procedure Method A2 (Mitsunobu Reaction in Solution: Scheme 1)

A solution of tert-butyl [(R)-1-hydroxy-4-(4-hydroxy-phenyl)-2-methyl-but-2-yl]-carbamate (1.48 g, 5 mmol), 4,4,5,5,5-pentafluoropentan-1-ol (0.74 ml, 5.5 mmol) and triphenyl phosphine (1.39 g, 5.25 mmol) in anhydrous THF (50 ml) is placed in an ice bath. After stirring for 10 min diethyl diazodicarboxylate (0.87 ml, 5.25 mmol) is injected slowly within a period of 15 min. After completion of the addition the ice bath is removed and the now pale yellow reaction mixture is stirred at RT under argon overnight. Then, the solvent is evaporated und the residue recrystallized from MTBE/hexane in order to remove most of the diethyl hydrazinodicarboxylate and triphenyl phosphine oxide formed in the reaction. The mother liquor is evaporated to dryness. Purification by flash chromatography (eluent:MTBE/Hexanes 1:2) affords the title compound as colorless crystals.

b) tert-Butyl [(R)-1-hydroxy-4-(4-hydroxy-phenyl)-2-methyl-but-2-yl]-carbamate The title compound can be prepared according to the scheme depicted below. As starting material Schoellkopf reagents either obtained from L-Valine and Alanine A or from D-Valine and Glycine B can be used.

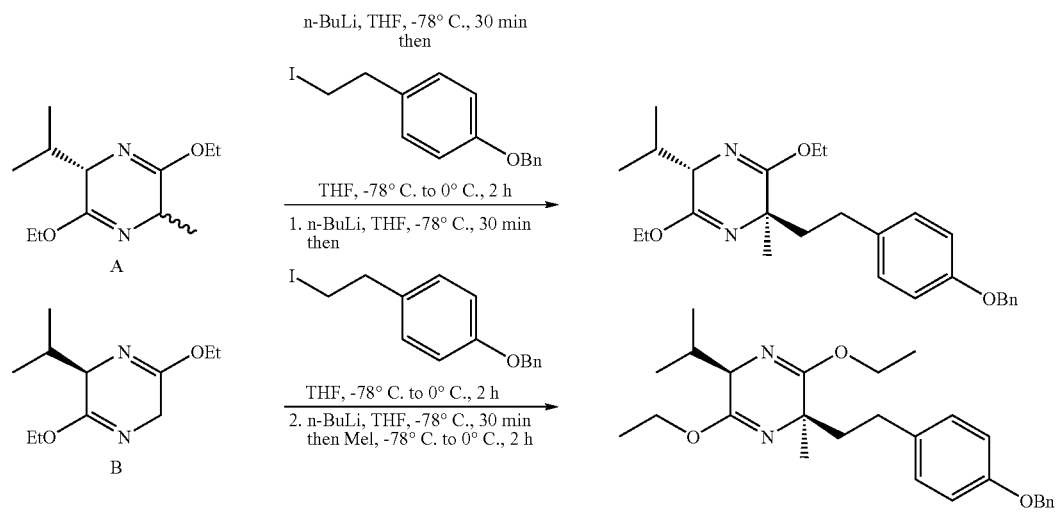

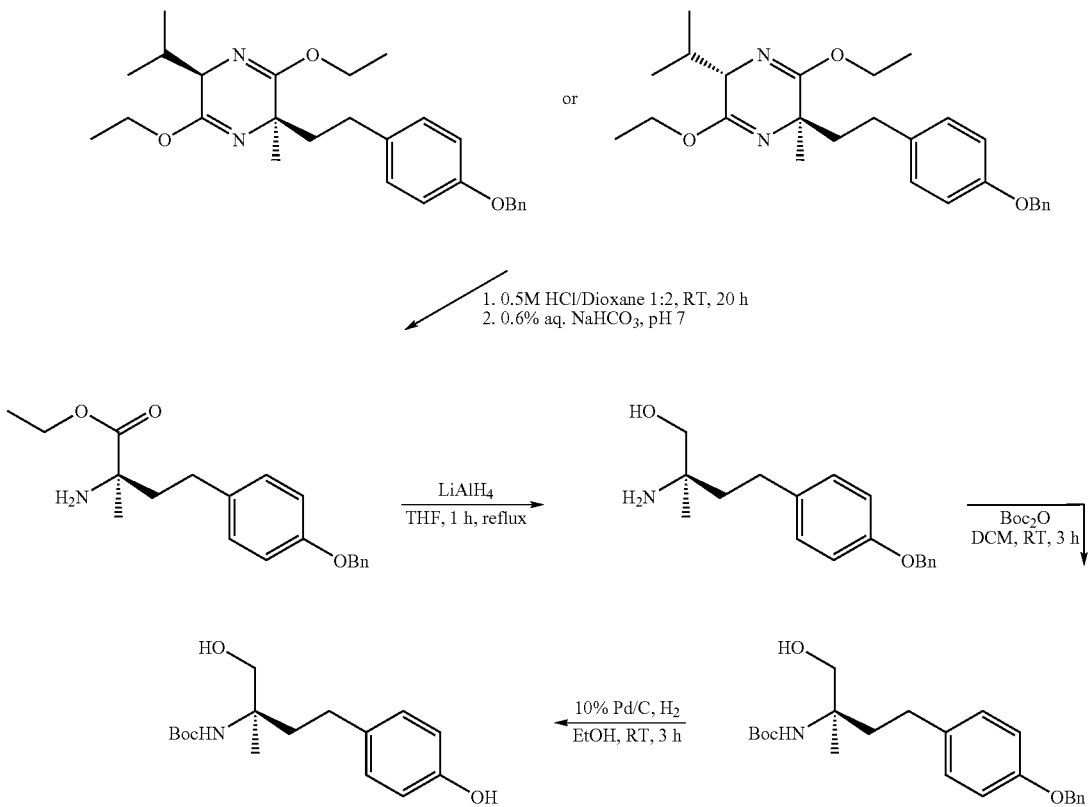

EXAMPLE 2

(R)-2-Amino-2-methyl-4-[4-(5-fluoro-pentyloxy)-phenyl]-butan-1-ol Hydrochloride

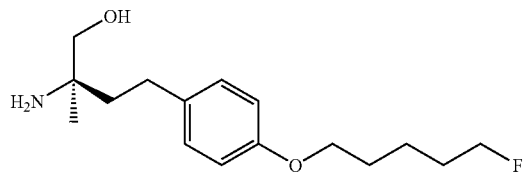

Deprotection of tert-butyl {(R)-1-Hydroxy-2-methyl-4-[4-(5-fluoro-pentyloxy)-phenyl]-but-2-yl carbamate performed as disclosed in Example 1 affords the title compound as a non hygroscopic off white powder: mp. 143-146° C., MS (ESI$^+$): 284 (MH$^+$), $^1$H-NMR (400 MHz, DMSO-d$_6$): δ 1.19 (s, 3H, 2-Me), 1.48 (cm, 2H, 3'-CH$_2$), 1.62-1.83 (m, 6H, 2'-, 3-, 4'-CH$_2$), 2.52 (cm, 2H, 4-CH$_2$), 3.39 (dd, 1H, $^2$J=10.1, $^3$J=5.3 1-CH$_\alpha$), 3.47 (dd, 1H, $^2$J=10.1, 3.3, 1-CH$_\beta$), 3.94 (t, 3H (t, 3H, $^3$J=6.6, 1'-OCH$_2$), 4.45 (dt, 2H, $^2$J$_{H,F}$=47.4, $^3$J$_{H,H}$=7.1, 5'-CH$_2$F, 5.51 (t, 1H, 1-OH), 6.85 ('d', 2H, J=8.9, ArH), 7.10 ('d', J=9.5 Hz, ArH), 7.78 (br s, 3H, 2-NH$_3^+$).

The required starting material may be prepared according to the following procedure:

a) tert-Butyl {(R)-1-hydroxy-2-methyl-4-[5-fluoro-pentyloxy)-phenyl]-but-2-yl}-carbamate General Procedure Method B1 (Alkylation Reaction: Scheme 1)

To a solution of tert-butyl [(R)-1-hydroxy-4-(4-hydroxyphenyl)-2-methyl-but-2-yl]-carbamate (200 mg, 0.68 mmol, Ex. 1b) and 1-bromo-5-fluoropentane (172 mg, 1.02 mmol, 1.5 eq.) in anhydrous DMF (2.5 ml) is added water free caesium carbonate (331 mg, 1.02 mmol, 1.5 eq.). The suspension obtained is stirred over night protected from moisture at 60° C. After cooling to RT the solids are filtered off and rinsed with DMF (2×1 ml). The combined filtrates are evaporated in a high vacuum to give a dark orange syrup. Purification by flash chromatography (FlashMaster II, MTBE/hexanes gradient as disclosed in Ex 1a)) gives colorless crystals: mp. 91-93° C., ESI+ MS: m/z=406 (MNa$^+$), 384 (MH$^+$), 328 (MH$^+$-tBu), $^1$H-NMR (400 MHz, CDCl$_3$): δ 1.23 (s, 3H, 2-Me), 1.46 (s, 9H, tBu), 1.60 (cm, 2H, 3'-CH$_2$), 1.74 (cm, 1H, 3-CH$_\alpha$), 1.77-1.90 (m, 4H, 2'- & 4'-CH$_2$), 2.03 (cm, 1H, 3-CH$_\beta$), 2.48-2.69 (m, 2H, 4-CH$_2$), 3.64 (br d, 1H, $^2$J=11.3, 1-CH$_\alpha$), 3.72 (br d, 1H, $^2$J=11.9, 1-CH$_\beta$), 3.96 (t, 2H, J=7.1, 1'-OCH$_2$), 4.03 (br, 1H, OH), 4.48 (dt, 2H, $^2$J$_{H,F}$=47.8, $^3$J$_{H,H}$=7.2, 5'-CH$_2$F), 4.62 (br s, 1H, NH), 6.80 ('d', 2H, J=10.1, ArH), 7.08 ('d', J=10.3, ArH).

EXAMPLES 3 TO 10

The following examples are prepared as described in example 2 (Method B1)

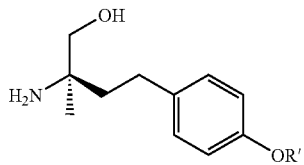

| example | wherein R' | MS (ESI$^+$): | appearance |
|---|---|---|---|
| 3 | —CH$_2$CH$_2$CH$_2$CH$_2$CH$_2$CH$_2$F | 320 (MNa$^+$), 298 (MH$^+$) | Off white powder |
| 4 | —CH$_2$CH$_2$CH$_2$CF$_3$ | 306 (MH$^+$) | Colorless crystalline powder |
| 5 | —CH$_2$CH$_2$CH$_2$CH$_2$CF$_3$ | 342 (MNa$^+$), 320 (MH$^+$) | Colorless crystalline powder |
| 6 | —CH$_2$CH$_2$CH$_2$CH$_2$CH$_2$CF$_3$ | 356 (MNa$^+$), 334 (MH$^+$) | Off white amorphous powder |
| 7 | —CH$_2$CH$_2$CH$_2$CF$_2$CH$_3$ | 302 (MH$^+$) | Off white powder |
| 8 | —CH$_2$CH$_2$CH$_2$CH$_2$CF$_2$CH$_3$ | 316 (MH$^+$) | Colorless amorphous powder |
| 9 | —CH$_2$CH$_2$—C$_6$H$_4$—Cl | 348/350 (MH$^+$). | Colorless microcrystalline powder |
| 10 | —CH$_2$CH$_2$CH$_2$CH(CH$_3$)$_2$ | 280 (MH$^+$) | Hygroscopic colorless powder |

EXAMPLES 11 TO 25

The following examples are prepared as described in example 1 (Method A1).

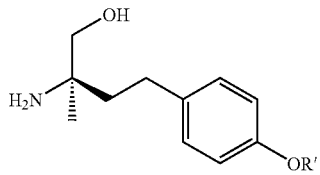

| example | wherein R' | MS (ESI): | appearance |
|---|---|---|---|
| 11 | —CH$_2$CH$_2$OCH$_2$CF$_3$ | 344 (MNa$^+$), 322 (MH$^+$) | Colorless powder |
| 12 | (difluorocyclopropyl-butyl) | 314 (MH$^+$) | Colorless powder |
| 13 | (trifluoro-alkenyl) | 318 (MH$^+$) | Off white powder |
| 12 | —CH$_2$CH$_2$—C$_6$H$_4$—OEt | 366 (MNa$^+$), 344 (MH$^+$) | Colorless microcrystalline powder |
| 14 | —CH$_2$CH$_2$—C$_6$H$_3$(OMe)$_2$ | 360 (MH$^+$) | Colorless amorphous powder |

-continued

Structure: HOCH₂-C(CH₃)(NH₂)-CH₂CH₂-C₆H₄-OR' (with stereochemistry at the quaternary carbon)

wherein R'

| example | R' | MS (ESI): | appearance |
|---|---|---|---|
| 15 | —CH₂CH₂—(2-naphthyl) | 350 (MH⁺). | Off white amorphous powder |
| 16 | —CH₂CH₂—(4-methylphenyl) | 314 (MH⁺) | Off white powder |
| 17 | —CH₂CH₂—(3-chlorophenyl) | 336 (MNa⁺), 314 (MH⁺) | Colorless amorphous powder |
| 18 | —CH₂CH₂—(phenyl) | 322 (MNa⁺), 300 (MH⁺). | Colorless amorphous powder |
| 19 | —CH₂CH₂—(3-methoxyphenyl) | 330 (MH⁺) | Off white amorphous powder |
| 21 | —CH₂CH₂—(2-chlorophenyl) | 334/336 (MH⁺) | Colorless microcrystalline powder |
| 22 | —CH₂CH₂—(3-trifluoromethylphenyl) | 390 (MNa⁺), 368 (MH⁺). | Colorless microcrystalline powder |
| 23 | —CH₂CH₂—(4-phenoxyphenyl) | 414 (MNa⁺), 392 (MH⁺). | Colorless amorphous powder |
| 24 | —CH₂CH₂—(4-trifluoromethylphenyl) | 390 (MNa⁺), 368 (MH⁺) | Off white amorphous powder |
| 25 | —CH₂CH₂—(4-trifluoromethoxyphenyl) | 406 (MNa⁺), 384 (MH⁺) | Off white amorphous powder |

EXAMPLE 26

(R)-2-Amino-4-{4-[2-(4-methoxy-phenyl)-ethoxy]-phenyl}-2-methyl-butan-1-ol

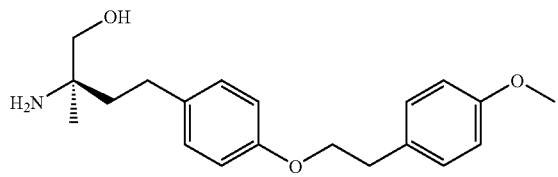

(R)-3-{4-[2-(4-methoxy-phenyl)-ethoxy]-phenyl}-1-hydroxymethyl-1-methyl-propyl)-carbamic acid tert-butyl ester (0.01 mol) is dissolved in dioxane (25 ml). After adding 5N HCl (25 ml), the mixture is left standing at RT for 6 h. The solvent is carefully removed by lyophilisation. MS (ESI+): 330 (MH+).

The required starting material may be prepared according to the following procedure:

(R)-3-{4-[2-(4-methoxy-phenyl)-ethoxy]-phenyl}-1-hydroxymethyl-1-methyl-propyl)-carbamic acid tert-butyl ester, General Procedure Method B2 (Alkylation Reaction: Scheme 1)

To a solution of tert-butyl [(R)-1-hydroxy-4-(4-hydroxyphenyl)-2-methyl-but-2-yl]-carbamate (0.1 mol) and methanesulfonic acid 4-methoxy-phenethyl ester (0.1 mol) in ethanol (500 ml) is added potassium carbonate (0.3 mol). The suspension is stirred at 70° C. for 16 h and cooled to RT. After filtration, the solvent is evaporated and the crude residue purified by chromatography using silica gel and CH$_2$Cl$_2$/MeOH=20/1 to give a white crystalline solid.

EXAMPLES 27 AND 28

The following examples are prepared as described in Example 20 (Method B2).

| example | wherein R' | MS (ESI) |
|---|---|---|
| 27 | —(CH$_2$)$_2$—[biphenyl] | 376 (MH+) |
| 28 | —(CH$_2$)$_2$—[biphenyl with MeO] | 406.5 (MH+) |

EXAMPLE 29

1-[4-((R)-3-Amino-hydroxy-3-methyl-butyl)-phenyl]-6,6,6-trifluoro-hexan-1-one

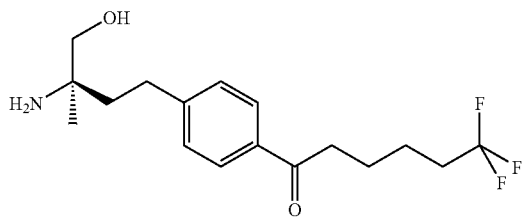

Deprotection of the corresponding N-{(R)-1-(tert-Butyl-dimethyl-silanyloxymethyl)-1-methyl-3-[4-(6,6,6-trifluoro-hexanoyl)-phenyl]-propyl}-acetamide is achieved in two steps by first stirring a solution of starting material (0.1 mmol) with tetrabutylammoniumfluoride (0.2 mmol) for 3 h at RT in THF. Quenching with water is followed by extraction with AcOEt, drying (MgSO$_4$) of the organic layer and evaporation of solvent.

The crude product is then dissolved in MeOH, water and THF and treated with LiOH (0.45 mmol) at 50° C. over night. Extraction with AcOEt, drying (MgSO$_4$) and evaporation of solvent is followed by crystallisation of the product from MeOH and diethyl ether. MS (ESI+): 332.4 (MH+).

The required starting material may be prepared according to the following procedure:

a) N-{(R)-1-(tert-Butyl-dimethyl-silanyloxymethyl)-1-methyl-3-[4-(6,6,6-trifluoro-1-hydroxyhexyl)-phenyl]-propyl}-acetamide To a solution of N-[(R)-1-(tert-Butyl-dimethyl-silanyloxymethyl)-3-(4-formyl-phenyl)-1-methylpropyl]-acetamide (0.1 mol) in dry THF is added a solution of 5-trifluoropentylmagnesium bromide (obtained from the corresponding bromide (0.45 mol) and magnesium turnings) in THF. After stirring at RT for 2 h, the reaction mixture is quenched with water and extracted with AcOEt (3x). The organic layer is washed with 1N HCl, saturated aqueous NaHCO$_3$ and water. After drying (MgSO$_4$) and evaporation of the solvent, the title compound is purified by chromatography using silica gel and AcOEt/hexanes=3/7.

b) N-{(R)-1-(tert-Butyl-dimethyl-silanyloxymethyl)-1-methyl-3-[4-(6,6,6-trifluoro-hexanoyl)-phenyl] propyl}-acetamide To a solution of oxalylchloride (0.15 mmol) in CH$_2$Cl$_2$ is added at −78° C. first DMSO (0.2 mmol) and then a solution of N-{(R)-1-(tert-Butyl-dimethyl-silanyloxymethyl)-1-methyl-3-[4-(6,6,6-trifluoro-1-hydroxy-hexyl)-phenyl]-propyl}-acetamide (0.1 mmol) in CH$_2$Cl$_2$. After stirring for 1 h at −78° C., triethylamine (0.7 mmol) is added and the mixture is warmed to RT. Quenching with water is followed by extraction with AcOEt. After drying (MgSO4), the solvent is evaporated.

EXAMPLES 30 TO 32

The following examples are deprotected as described in Example 29. The required starting materials are prepared according to example 29 using the appropriate Grignard reagents.

| example | wherein R'' | MS (ESI) |
|---|---|---|
| 30 | ![structure] CH3-CO-(CH2)4-CF3 | 346.4 (MH+) |
| 31 | ![structure] CH3-CO-CH2-CH2-C6H4-C6H5 | 388.5 (MH+) |
| 32 | —(CH2)3—C6H4—C6H5 | 374.5 (MH+) |

EXAMPLE 33

(R)-2-Amino-2-methyl-4-[4-(7,7,7-trifluoro-heptyl)-phenyl]-butan-1-ol

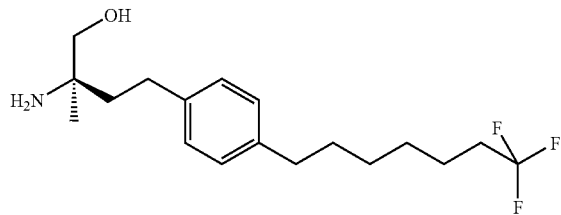

Deprotection of the corresponding N-{(R)-1-(tert-Butyl-dimethyl-silanyloxymethyl)-1-methyl-3-[4-(7,7,7-trifluoro-heptyl)-phenyl]-propyl}-acetamide is performed as disclosed in Example 29. MS (ESI+): 332.4 (MH+)

The required starting material is prepared according to example 29, using the appropriate Grignard reagent in step a). Instead of step b) the corresponding alcohol is acetylated using acetic anhydride in pyridine, followed by hydrogenolysis in EtOH using hydrogen at 1 bar and 10% Pd on charcoal.

EXAMPLE 34

Mono-(R)-2-Amino-2-methyl-4-[4-(4,4,5,5,5-pentafluoro-pentyloxy)-phenyl]-but-2-yl phosphate

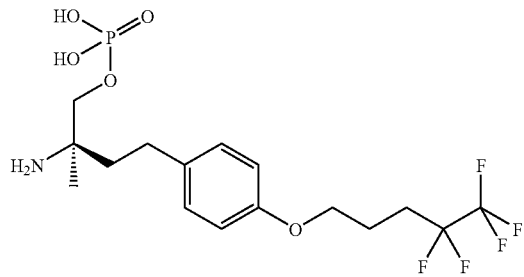

General Procedure Method C1 (Scheme 2)

To a solution of tert-butyl {(R)-2-Methyl-2-(3-oxo-1,5-dihydro-3λ$^5$-benzo[e][1,3,2]dioxaphosphepin-3-yloxy)-4-[4-(4,4,5,5,5-pentafluoro-pentyloxy)-phenyl]-but-2-yl}-carbamate (32 mg, 0.05 mmol) in methanol is added Pd/C 10% (50 mg). The suspension is purged with nitrogen and then hydrogenated at atmospheric pressure with gentle stirring for 2 h. Thereafter, the catalyst is filtered off and the filtrate is evaporated to dryness to give a colorless resin. The residue is re-dissolved in dioxane (0.75 ml) and 4 M HCl in dioxane (0.25 ml) is added. After stirring for 2 h the slightly turbid solution is evaporated. The colorless semi-solid residue is sonicated with dry ether (5 ml) to give a colorless precipitate. The solid is filtered off, washed with dry ether and vacuum dried to afford a colorless powder: mp. 229-231° C., MS (ESI+): 434 (M–H−), $^1$H-NMR (400 MHz, CD$_3$OD): δ 1.37 (s, 3H, 2-Me), 1.88 (cm, 1H, 3-CH$_\alpha$), 1.94-2.09 (m, 3H, 3-CH$_\alpha$+2'-CH$_2$), 2.32 (cm, 2H, 3'-CH$_2$), 2.64 (cm, 2H, 4-CH$_2$Ar), 3.90 (dd, 1H, $^2$J=10.6, $^3$J$_{H,P}$=4.5, 1-CH$_\alpha$), 4.00 (dd, 1H, 1-CH$_\beta$), 4.03 (t, 3H, $^3$J=6.6 Hz, 1'-ArOCH$_2$), 6.88 ('d', 2H, J=10.1, ArH), 7.16 ('d', J=8.1, ArH).

The required starting material can be prepared according to the following procedure:

a) tert-butyl {(R)-2-Methyl-2-(3-oxo-1,5-dihydro-3λ$^5$-benzo[e][1,3,2]dioxaphos-phepin-3-yloxy)-4-[4-(4,4,5,5,5-pentafluoro-pentyloxy)-phenyl]-but-2-yl}-carbamate To a solution of tert-butyl {(R)-1-hydroxy-2-methyl-4-[4-(4,4,5,5,5-pentafluoro-pentyloxy)-phenyl]-but-2-yl}-carbamate (40 mg, 0.088 mmol, Ex. 1a) and tetrazole (18 mg, 0.26 mmol, 3 eq., recrystallized from toluene) in dry THF (1 ml) is added 3-diethylamino-1,5-dihydrobenzo[e][1,3,2]dioxaphosphepine (32 μl, 0.13 mmol, 1.5 eq.). The reaction mixture is stirred under argon at RT for 3 h. Then, H$_2$O$_2$ (30%, 90 μl, 0.88, 10 eq.) is injected at 0° C. with vigorous stirring. The reaction mixture is stirred for further 30 min, followed by addition of saturated sodium thiosulfate solution (1 ml). The organic layer is separated and the aqueous phase is extracted with ether (3×1 ml). The combined organic extracts are washed with brine, dried over MgSO$_4$, and evaporated to dryness. The crude material is purified by flash chromatography (MTBE/hexane 1:1) to afford colorless crystals: MS (ESI+): 655 (MNH$_4$+), 638 (MH+), 538 (MH+-Boc). $^1$H-NMR (400 MHz, CDCl$_3$): δ 1.36 (s, 3H, 2-Me), 1.44 (s, 9H, tBu), 1.80 (cm, 1H, 3-CH$_\alpha$), 2.02-2.20 (m, 3H, 3-CH$_\alpha$+ 2'-CH$_2$), 2.27 (cm, 2H, 3'-CH$_2$), 2.59 ('t', 2H, J=8.6, 4-CH$_2$Ar), 4.02 (t, 3H, $^3$J=5.9, 1'-ArOCH$_2$), 4.17 (dd, 1H, $^2$J=9.9, $^3$J$_{H,P}$=5.4, 1-CH$_\alpha$), 4.35 (dd, 1H, 1-CH$_\beta$), 5.17 (dd, 2H, ArCH$_2$O, $^2$J=13.6, $^3$J$_{H,P}$=5.3), 5.30 (ddd, 2H, ArCH$_\beta$O, $^2$J=13.4, $^3$J$_{H,P}$=16.3, J=4.4), 6.82 ('d', 2H, J=8.9, ArH), 7.16 ('d', J=8.7, ArH), 7.29-7.35 (m, 2H, ArH), 7.37-7.42 (m, 2H, ArH).

EXAMPLE 35

Mono-(R)-2-Amino-2-methyl-4-[4-(5-fluoro-pentyloxy)-phenyl]-but-2-yl phosphate

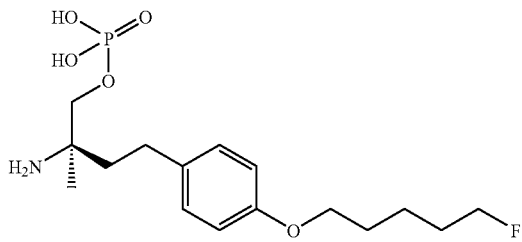

General Procedure Method C2 (Scheme 2)

To a solution of tert.-butyl {(R)-1-(di-tert.-butoxy-phosphoryloxymethyl)-3-[4-(5-fluoropentyloxy)-phenyl]-1-methyl-propyl}-carbamate (90 mg, 0.16 mmol) in dioxane (0.75 ml) is added 4M HCl in dioxane (0.25 ml). After stirring for 2 h the cloudy solution is evaporated. The colorless waxy residue is sonicated with dry ether (5 ml) to give a beige precipitate. The solid is filtered off, washed with dry ether and vacuum dried to afford a tan powder: mp. 237-241° C., MS (ESI$^+$): 727 (M$_2$H$^+$), 364 (MH$^+$), $^1$H-NMR (400 MHz, CD$_3$OD): δ 1.37 (s, 3H, 2-Me), 1.60 (cm, 2H, 3'-CH$_2$), 1.69-1.93 (m, 5H, 3-CH$_α$ & 2'-CH$_2$ & 4'-CH$_2$), 2.01 (cm, 2H, 3-CH$_β$), 2.55-2.75 (m, 2H, 4-CH$_2$Ar), 3.86 (dd, 1H, 2J=10.3, $^3$J$_{H,P}$=4.6, 1-CH$_α$), 3.97 (dd, 1H, 1-CH$_β$), 3.99 (t, 3H, $^3$J=6.8 Hz, 1'-ArOCH$_2$), 4.46 (dt, 2H, $^2$J$_{H,F}$=46.2, $^3$J$_{H,H}$=6.9, 5'-CH$_2$F), 6.84 ('d', 2H, J=10.4, ArH), 7.16 ('d', J=8.5, ArH).

The required starting material can be prepared according to the following procedure:

a) tert.-butyl {(R)-1-(di-tert.-butoxy-phosphoryloxymethyl)-3-[4-(5-fluoropentyloxy)-2-phenyl]-1-methyl-propyl}-carbamate To a solution of tert-butyl {(R)-1-hydroxy-2-methyl-4-[4-(5-fluoro-pentyloxy)-phenyl]-but-2-yl}-carbamate (80 mg, 0.21 mmol, Ex. 2a) and tetrazole (88 mg, 1.26 mmol, 6 eq., recrystallized from toluene) in dry THF (2 ml) is added di-tert.-butyl diethylphosphoramidite (174 μl, 0.63 mmol, 3 eq.). The reaction mixture is stirred under argon at RT for 2 h. After addition of triethylamine (320 ml, 2.3 mmol, 11 eq.) hydrogen peroxide (30%, 213 μl, 2.1 mmol, 10 eq.) is injected at 0° C. with vigorous stirring. The reaction mixture is stirred for further 30 min, followed by addition of saturated sodium thiosulfate solution (1 ml). The organic layer is separated and the aqueous phase is extracted with ether (3×1 ml). The combined organic extracts are washed with brine, dried over MgSO$_4$, and evaporated to dryness. The crude material is purified by flash chromatography (MTBE/Hx 1:1) to afford colorless crystals: MS (ESI$^+$): 598 (MNa$^+$), 593 (MNH$_4^+$), 576 (MH$^+$), $^1$H-NMR (400 MHz, CDCl$_3$): δ 1.37 (s, 3H, 2-Me), 1.46 (s, 9H, Boc), 1.52 (s, 18H, tBuO), 1.62 (cm, 2H, 3'-CH$_2$), 1.70-1.98 (m, 5H, 3-CH$_α$ & 2'-CH$_2$ & 4'-CH$_2$), 2.08 (cm, 1H, 3-CH$_β$), 2.48 (cm, 2H, 4-CH$_2$Ar), 3.88 (dd, 1H, $^2$J=10.1, $^3$J$_{H,P}$=5.5, 1-CH$_α$), 3.96 (t, 3H, $^3$J=6.5, 1'-ArOCH$_2$), 4.07 (dd, 1H, 1-CHP), 4.44 (dt, 2H, $^2$J$_{H,F}$=44.2, $^3$J$_{H,H}$=6.7, 5'-CH$_2$F), 6.82 ('d', 2H, J=9.1, ArH), 7.10 ('d', J=8.9, ArH).

EXAMPLES 36 TO 44

The following examples are prepared as described in Method C2.

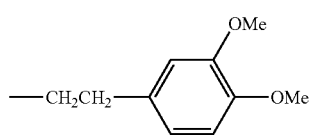

| example | wherein R' | MS (ESI): | appearance |
|---|---|---|---|
| 36 | —CH$_2$CH$_2$CH$_2$CH$_2$CH$_2$CH$_2$F | 400 (MNa$^+$), 378 (MH$^+$) | Colorless powder |
| 37 | —CH$_2$CH$_2$CH$_2$CF$_3$ | 408 (MNa$^+$), 386 (MH$^+$) | Colorless powder |
| 38 | —CH$_2$CH$_2$CH$_2$CH$_2$CF$_3$ | 400 (MH$^+$) | Tan, fluffy powder |
| 39 | —CH$_2$CH$_2$CH$_2$CH$_2$CH$_2$CF$_3$ | 436 (MNa$^+$), 414 (MH$^+$) | Tan amorphous powder |
| 40 | —CH$_2$CH$_2$CH$_2$CF$_2$CH$_3$ | 763 (M$_2$H$^+$), 404 (MNa$^+$), 382 (MH$^+$) | Colorless powder |
| 41 | —CH$_2$CH$_2$-(2-OMe, 4-OMe-phenyl) | 440 (MH$^+$) | Colorless microcrystalline powder |
| 42 | —CH$_2$CH$_2$-(naphthyl) | 430 (MH$^+$) | Tan amorphous powder |

-continued

| example | wherein R' | MS (ESI): | appearance |
|---|---|---|---|
| 43 | —CH₂CH₂—(3-OMe-phenyl) | 432 (MNa⁺), 410 (MH⁺) | Colorless microcrystalline powder |
| 44 | —CH₂CH₂—(3-Cl-phenyl) | 414 (MH⁺). | Tan amorphous powder |

EXAMPLES 45 TO 51

The following examples are prepared as described in Method C1.

| example | wherein R'' | MS (ESI): |
|---|---|---|
| 45* | —OCH₂CH₂—(4-OEt-phenyl) | 869 (M₂Na⁺), 847 (M₂H⁺), 446 (MNa⁺), 424 (MH⁺) |
| 46* | —OCH₂CH₂—(4-OMe-phenyl) | 410 (MH⁺) |
| 47 | —OCH₂CH₂—(4-Cl-phenyl) | 412 (M – H⁻) |
| 48 | —O—CH₂CH₂CH₂CH(CH₃)₂ | 360 (M – H⁺) |
| 49 | —O(CH₂)₃—(biphenyl) | 454 (M – H⁻) |
| 50 | CH₃C(O)CH₂CH₂—(biphenyl) | 466.5 (M – H⁻) |
| 51 | CH₃C(O)CH₂CH₂CH₂CH₂CF₃ (with two F) | 424.4 (M – H⁻) |

*= colorless powder

EXAMPLE 52

2-Amino-2-{2-[4-(4,4,4-trifluoro-butoxy)-phenyl]-ethyl}-propane-1,3-diol

General Procedure Method F (Scheme 3)

To a solution of 2-methyl-4-{2-[4-(4,4,4-trifluoro-butoxy)-phenyl]-ethyl}-4,5-dihydro-oxazol-4-yl)-methanol (200 mg, 0.57 mmol) in ethanol (5 ml) is added conc. hydrochloric acid (5 ml). The reaction mixture is stirred at 85° C. for 4 hours, then concentrated to dryness. The residue is re-dissolved in AcOEt and precipitated with hexanes. The solid is filtered off, washed with dry ether and dried under vacuum to afford hydrochloric salt of 2-amino-2-{2-[4-(4,4,4-trifluoro-butoxy)-phenyl]-ethyl}propane-1,3-diol as a white powder. MS (ESI+): 322.2 (MH+)

The required starting material may be prepared according to the following procedure:

a) 2-Methyl-4-{2-[4-(4,4,4-trifluoro-butoxy)-phenyl]-ethyl}-4,5-dihydro-oxazol-4-yl)-methanol (General Procedure Method D, Scheme 3)

To a solution of 4-[2-(4-hydroxymethyl-2-methyl-4,5-dihydro-oxazol-4-yl)-ethyl]-phenol (500 mg, 2.12 mmol) in dry DMF (8 ml) is added under inert atmosphere $Cs_2CO_3$ (901 mg, 2.76 mmol, 1.3 eq.) and 4-bromo-1,1,1-trifluoro-butane (487.8 mg, 2.55 mmol, 1.2 eq.). The reaction mixture was stirred under inert atmosphere at 85° C. overnight. A saturated solution of $NaHCO_3$ (20 ml) and AcOEt (40 ml) were then added. The organic layer is separated and the aqueous phase is extracted with AcOEt (3×40 ml). The combined organic extracts are washed with brine and 1M HCl, dried over $MgSO_4$, and evaporated to dryness. Purification by flash chromatography (cy Hexane/AcOEt (9/1) to (1/1) and (0/1)) affords 2-methyl-4-{2-[4-(4,4,4-trifluoro-butoxy)-phenyl]-ethyl}-4,5-dihydro-oxazol-4-yl)-methanol as colorless oil.

b) 4-[2-(4-hydroxymethyl-2-methyl-4,5-dihydro-oxazol-4-yl)-ethyl]-phenol

The title compound can be prepared according to the scheme depicted below.

To a solution of 2-(4-benzyloxy-phenyl)-ethanol (78.72 g, 0.34 mol) in methylene chloride (400 ml) is added triethylamine (67.3 ml, 0.44 mol, 1.4 eq), then at 0° C. is added mesylchloride (34.8 ml, 0.44 mol, 1.3 eq). The reaction mixture is stirred at 0° C. for 30 minutes and allowed to rise to room temperature. The reaction mixture is extracted with methylene chloride (2×300 ml), the combined organic layers are then washed with brine (2×300 ml) and concentrated under vacuum. To the crude product in solution in AcOEt (600 ml) is added sodium iodide (67.2 g, 0.44 mol, 1.3 eq) and the reaction mixture is stirred under reflux for 6 hours. After filtration, the organic layer is washed with brine (3×400 ml), dried with $Na_2SO_4$, filtered and concentrated under vacuum. 1-Benzyloxy-4-(2-iodo-ethyl)-benzene is isolated after crystallization with diethyl ether.

To a solution of acetamidomalonate (59.4 g, 0.27 mol, 2 eq) in dry dimethylformamide (400 ml) is added at 0° C. under inert atmosphere sodium hydride (60% in oil) (9.94 g, 0.49 mol, 1.8 eq), the reaction mixture is stirred for 3 hours at 0° C. 1-Benzyloxy-4-(2-iodo-ethyl)-benzene (46.8 g, 0.13 mol, 1 eq) in solution in dry DMF (250 ml) is then slowly added at 0° C. and the reaction mixture is stirred at room temperature overnight. The reaction mixture is quenched with few drops of methanol and concentrated almost to dryness under vacuum, then extracted with AcOEt and washed subsequently with 1N HCl (2×500 ml), saturated solution of $NaHCO_3$ (2×500 ml) and brine (2×500 ml), dried with $Na_2SO_4$, filtered and concentrated under vacuum. 2-Acetylamino-2-[2-(4-benzyloxy-phenyl)-ethyl]-malonic acid diethyl ester is isolated after multiple crystallization using diethyl ether.

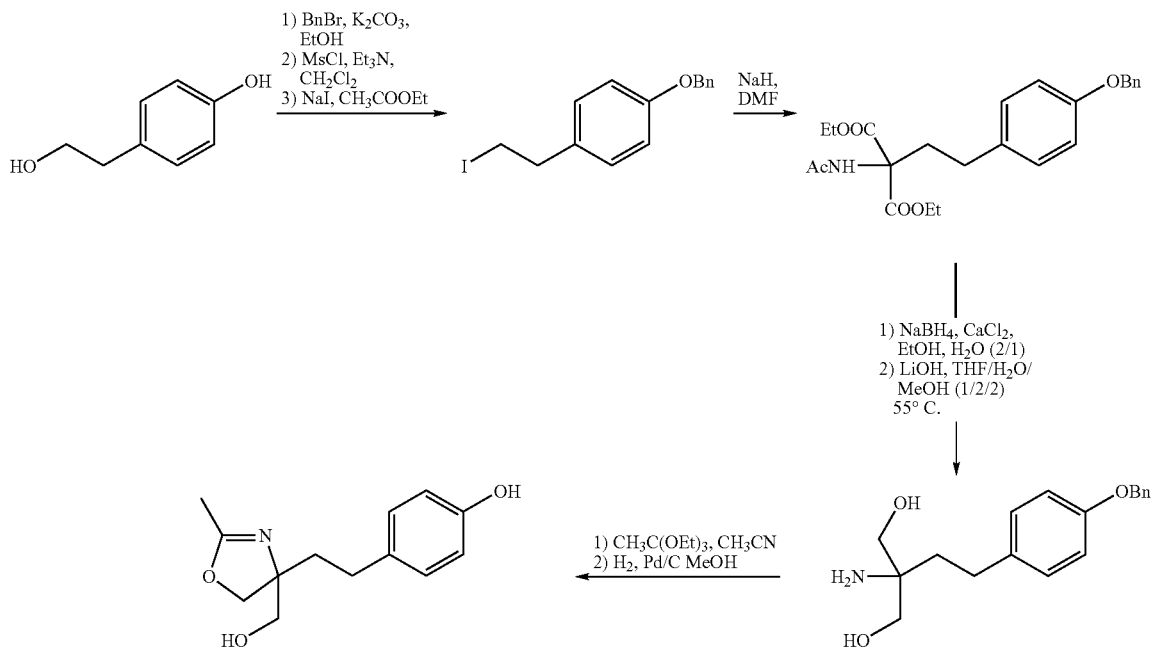

To a solution of 4-(2-hydroxy-ethyl)-phenol (50 g, 0.36 mol) in ethanol (400 ml) is added potassium carbonate (75 g, 0.54 mol, 1.5 eq) and benzyl bromide (47.2 ml, 0.39 mol, 1.1 eq), the reaction mixture is stirred at room temperature overnight. The reaction mixture is then filtered off through celite and concentrated under vacuum. 2-(4-Benzyloxy-phenyl)-ethanol is isolated after crystallization with diethyl ether.

To a solution of 2-acetylamino-2-[2-(4-benzyloxy-phenyl)-ethyl]-malonic acid diethyl ester (44.1 g, 0.1 mol) in ethanol water (2/1) (285 ml/285 ml) is added $CaCl_2$ (28.5 g, 0.26 mol, 2.5 eq) and $NaBH_4$ by portion (19.4 g, 0.52 mol, 5.0 eq), the reaction mixture is stirred overnight at room temperature. At 0° C. the reaction mixture is carefully quenched with drop wise methanol (10 ml) and concentrated to almost dryness under vacuum. The crude mixture is extracted with AcOEt (4×500 ml) and washed subsequently with 1N HCl (2×300 ml), saturated solution of NaHCO$_3$ (2×300 ml) and brine (2×300 ml). The combined organic layers are then dried with Na$_2$SO$_4$, filtered and concentrated under vacuum. N-[3-(4-benzyloxy-phenyl)-1,1-bis-hydroxymethyl-propyl]-acetamide is carried on without further purification.

To a solution of crude N-[3-(4-benzyloxy-phenyl)-1,1-bis-hydroxymethyl-propyl]-acetamide in a mixture of tetrahydrofuran, methanol, water (1/2/2) (450 ml/900 ml/900 ml) is added at room temperature lithium hydroxide (32.7 g, 1.36 mol, 8.0 eq). The reaction mixture is stirred at 55° C. for 5 hours, then extracted with AcOEt (500 ml) and washed with brine (2×300 ml), the combined organic layers are then dried with Na$_2$SO$_4$, filtered and concentrated under vacuum. 2-Amino-2-[2-(4-benzyloxy-phenyl)-ethyl]-propane-1,3-diol is isolated after crystallization using AcOEt.

To a solution of 2-amino-2-[2-(4-benzyloxy-phenyl)-ethyl]-propane-1,3-diol (31.1 g, 0.10 mol) in acetonitrile (2.38 l) is added triethylortho acetate (17.1 ml, 0.12 mol, 1.2 eq) and acetic acid (5.48 ml, 0.11 mol. 1.1 eq), the reaction mixture is then stirred at 80° C. for 5 hours. The reaction mixture is then concentrated under vacuum, {4-[2-(4-benzyloxy-phenyl)-ethyl]-2-methyl-4,5-dihydro-oxazol-4-yl}-methanol is isolated after crystallization with AcOEt.

To a solution of {4-[2-(4-benzyloxy-phenyl)-ethyl]-2-methyl-4,5-dihydro-oxazol-4-yl}-methanol (26.1 g, 0.08 mol) in methanol (800 ml) is added palladium on charcoal (2.6 g, 10% wt), and the reaction mixture is stirred under hydrogen atmosphere at room temperature for 5 hours. The reaction mixture is then filtered through celite and concentrated under vacuum. 4-[2-(4-Hydroxymethyl-2-methyl-4,5-dihydro-oxazol-4-yl)-ethyl]-phenol is isolated after crystallization with AcOEt and hexanes.

EXAMPLES 3 TO 59

The following examples are prepared as described in Method D and F.

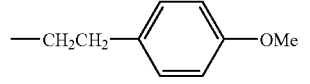

| example | wherein R' | MS (ESI) |
|---|---|---|
| 53 | —CH$_2$CH$_2$CH$_2$CH$_2$CH$_2$F | 300.3 (MH$^+$) |
| 54 | —CH$_2$CH$_2$CH$_2$CF$_2$CH$_3$ | 318.2 (MH$^+$) |
| 55 | —CH$_2$CH$_2$CH$_2$CH$_2$CF$_3$ | 336.2 (MH$^+$) |
| 56 | —CH$_2$CH$_2$CH$_2$CF$_2$CF$_3$ | 372.2 (MH$^+$) |
| 57 | —CH$_2$CH$_2$CH$_2$CH$_2$CH$_2$CH$_2$F | 314.3 (MH$^+$) |
| 58 | —CH$_2$CH$_2$CH$_2$CH$_2$CF$_2$CH$_3$ | 332.2 (MH$^+$) |
| 59 | —CH$_2$CH$_2$CH$_2$CH$_2$CF$_2$CF$_3$ | 350.3 (MH$^+$) |

EXAMPLES 60 TO 62

The following examples are prepared as described in Method D with the mesylate instead of the bromide as alkylating agent and in method F.

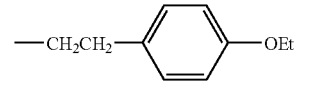

| example | wherein R' | MS (ESI) |
|---|---|---|
| 60 | —CH$_2$CH$_2$—⟨phenyl⟩—OMe | 346.3 (MH$^+$) |
| 61 | —CH$_2$CH$_2$—⟨phenyl⟩—OEt | 360.3 (MH$^+$) |
| 62 | —CH$_2$CH$_2$—⟨phenyl⟩—Cl | 350.2 (MH$^+$) |

EXAMPLE 63

2-Amino-2-(2-{4-[2-(4-methoxy-3-fluoro-phenyl)-ethoxy]-phenyl}-ethyl)-propane-1,3-diol

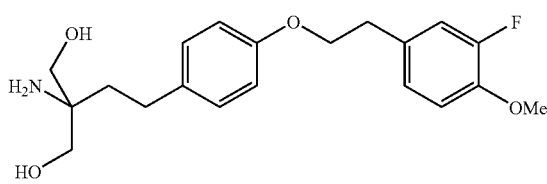

General Procedure Method E (Scheme 3).

To a solution of 4-[2-(4-hydroxymethyl-2-methyl-4,5-dihydro-oxazol-4-yl)-ethyl]-phenol (300 mg, 1.27 mmol) in dry THF (6 ml) is added under inert atmosphere polystyrene supported triphenylphosphine (loading 3 mmol·g$^{-1}$, 1.27 g, 3.81 mmol, 3 eq.), 2-(3-fluoro-4-methoxyphenyl)-ethanol (647.7 mg, 3.81 mmol, 3 eq.) and DBAD (877.3 mg, 3.81 mmol, 3 eq.). The reaction mixture was stirred under inert atmosphere at room temperature overnight. Polystyrene supported triphenylphosphine was then filtered through frit and washed with ethyl acetate and methanol. The reaction mixture was then concentrated to dryness following by addition of 4M HCl in dioxane (3 ml), the reaction was stirred at room temperature for 3 hours. The reaction mixture was quenched by addition of saturated solution of NaHCO$_3$ (10 ml) and ethyl acetate (40 ml). The organic layer is separated and the aqueous phase is extracted with ethyl acetate (3×40 ml). The combined organic extracts are washed with brine, dried over MgSO$_4$, and evaporated to dryness. Purification using Flashmaster (chexane/ethyl acetate (1/9), ethyl acetate and ethyl acetate/methanol (98/2)) affords [4-(2-{4-[2-(3-fluoro-4-methoxy-phenyl)-ethoxy]-phenyl}ethyl)-2-methyl-4,5-dihydro-oxazol-4-yl]-methanol as colorless oil. MS (ESI$^+$): 364.2 (MH$^+$)

EXAMPLES 64 TO 78

The following examples are prepared as described in Method E and F.

| example | wherein R' | MS (ESI) |
|---|---|---|
| 64 | —CH₂CH₂—(2,4-diOMe-C₆H₃) wait — 2-OMe, 4-OMe phenyl (actually 3,4-diOMe per image: OMe at top, OMe at right) | 410.2 (MH⁺) |
| 65 | —CH₂CH₂—(3-OMe-C₆H₄) | 346.4 (MH⁺) |
| 66 | —CH₂CH₂—(3-OEt-C₆H₄) | 360.2 (MH⁺) |
| 67 | —CH₂CH₂—C₆H₅ | 316.1 (MH⁺) |
| 68 | —CH₂CH₂—(4-Me-C₆H₄) | 330.2 (MH⁺) |
| 69 | —CH₂CH₂—(2-Me-C₆H₄) | 330.2 (MH⁺) |
| 70 | —CH₂CH₂—(2-naphthyl) | 366.2 (MH⁺) |
| 71 | —CH₂CH₂—(4-biphenyl) | 392.2 (MH⁺) |
| 72 | —CH₂CH₂—(3-Cl-4-OEt-C₆H₃) | 394.2 (MH⁺) |
| 73 | —CH₂CH₂—(3-MeO-4-OMe-C₆H₃) | 376.0 (MH⁺) |
| 74 | —CH₂CH₂—(4-CF₃-C₆H₄) | 384.3 (MH⁺) |
| 75 | —CH₂CH₂—(4-F-C₆H₄) | 334.3 (MH⁺) |
| 76 | —CH₂CH₂—(2,3-diOMe-C₆H₃) | 376.6 (MH⁺) |
| 77 | —CH₂CH₂—(3-Br-4-OMe-C₆H₃) | 424.2 and 426.2 (MH⁺) |
| 78 | —CH₂CH₂—(3,5-diOMe-C₆H₃) | 376.2 (MH⁺) |

EXAMPLE 79

Mono-{2-amino-2-hydroxymethyl-4-[4-(6,6,6-trifluoro-hexyloxy)-phenyl]-butyl}ester phosphate

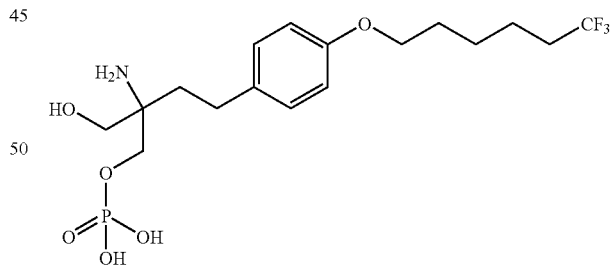

General Procedure Method G (Scheme 3)

To a solution of (2-Methyl-4-{2-[4-(6,6,6-trifluoro-hexyloxy)-phenyl]-ethyl}-4,5-dihydro-oxazol-4-yl)-methanol (300 mg, 0.80 mmol) and tetrazole (337.4 mg, 4.82 mmol, 6 eq., recrystallized from toluene) in dry THF (6 ml) is added 3-diethylamino-1,5-dihydrobenzo[e]-[1,3,2]dioxaphosphepine (433.5 µl, 1.56 mmol, 1.95 eq.). The reaction mixture is stirred under argon at room temperature for 3 h. Then, H₂O₂ (30%, 75 µl, 4.0 mmol, 5 eq.) is injected at 0° C. with vigorous stirring. The reaction mixture is stirred for further 30 min, followed by addition of saturated sodium thiosulfate solution (1 ml). The organic layer is separated and the aqueous phase is extracted with ether (3×20 ml). The combined organic extracts are washed with brine, dried over MgSO$_4$, and evaporated to dryness. Purification by flash chromatography (AcOEt) affords phosphoric acid di-tert-butyl ester 2-methyl-4-{2-[4-(6,6,6-trifluoro-hexyloxy)-phenyl]-ethyl}-4,5-dihydro-oxazol-4-ylmethyl ester as colorless oil. To a solution of phosphoric acid di-tert-butyl ester 2-methyl-4-{2-[4-(6,6,6-trifluoro-hexyloxy)-phenyl]-ethyl}-4,5-dihydro-oxazol-4-ylmethyl ester (33 mg, 0.050 mmol) in ethanol (2 ml) is added conc. HCl (2 ml). The reaction mixture is stirred at 85° C. for 2 hours, then concentrated to dryness. The residue is re-dissolved in AcOEt and precipitated with hexanes. The solid is filtered off, washed with dry ether and dried under vacuum to afford phosphoric acid mono-{2-amino-2-hydroxymethyl-4-[4-(6,6,6-trifluoro-hexyloxy)-phenyl]-butyl}ester as a colorless powder. MS (ESI$^-$): 428.2 (MH$^-$)

EXAMPLES 80 TO 95

The following examples are prepared as described in Method G.

| example | wherein R' | MS (ESI) |
|---|---|---|
| 80 | —CH$_2$CH$_2$CH$_2$CF$_3$ | 402.3 (MH$^+$) |
| 81 | —CH$_2$CH$_2$CH$_2$CH$_2$CH$_2$F | 378.2 (MH$^-$) |
| 82 | —CH$_2$CH$_2$CH$_2$CF$_2$CH$_3$ | 396.2 (MH$^-$) |
| 83 | —CH$_2$CH$_2$CH$_2$CH$_2$CF$_3$ | 414.2 (MH$^-$) |
| 84 | —CH$_2$CH$_2$CH$_2$CF$_2$CF$_3$ | 450.2 (MH$^-$) |
| 85 | —CH$_2$CH$_2$CH$_2$CH$_2$CH$_2$CH$_2$F | 394.3 (MH$^+$) |
| 86 | —CH$_2$CH$_2$CH$_2$CH$_2$CF$_2$CH$_3$ | 412.2 (MH$^+$) |
| 87 | —CH$_2$CH$_2$—C$_6$H$_4$—OMe | 438.2 (MH$^-$) |
| 88 | —CH$_2$CH$_2$—C$_6$H$_4$—OEt | 376.6 (MH$^+$) |
| 89 | —CH$_2$CH$_2$—C$_6$H$_4$—Cl | 430.1 (MH$^+$) |
| 90 | —CH$_2$CH$_2$—C$_6$H$_4$—OMe (meta) | 426.4 (MH$^+$) |
| 91 | —CH$_2$CH$_2$—C$_6$H$_4$—OEt (meta) | 438.2 (MH$^-$) |
| 92 | —CH$_2$CH$_2$—C$_6$H$_4$—CH$_3$ | 410.0 (MH$^+$) |
| 93 | —CH$_2$CH$_2$—C$_6$H$_3$(Cl)—OEt | 474.2 (MH$^+$) |
| 94 | —CH$_2$CH$_2$—C$_6$H$_3$(F)—OMe | 442.2 (MH$^-$) |
| 95 | —CH$_2$CH$_2$—C$_6$H$_3$(OMe)$_2$ | 454.2 (MH$^-$) |

The compounds of formula I in free form or in pharmaceutically acceptable salt form, exhibit valuable pharmacological properties, e.g. lymphocyte recirculation modulating properties, e.g. as indicated in in vitro and in vivo tests and are therefore indicated for therapy.

A. In Vitro

The compounds of formula I have binding affinity to individual human S1P receptors as determined in following assays:

Sphingosine-1-Phosphate (S1P) Receptor Profiling

Agonist activities of compounds are tested on the human S1P receptors (S1P$_1$), (S1P$_3$), (S1P$_2$), (S1P$_4$) and (S1P$_5$). Functional receptor activation is assessed by quantifying compound induced GTP [γ-$^{35}$S] binding to membrane protein prepared from transfected CHO or RH7777 cells stably expressing the appropriate human S1P receptor. The assay technology used is SPA (scintillation proximity based assay). Briefly, DMSO dissolved compounds are serially diluted and added to SPA-bead (Amersham-Pharmacia) immobilised S1P receptor expressing membrane protein (10-20 μg/well) in the presence of 50 mM Hepes, 100 mM NaCl, 10 mM MgCl$_2$, 10 μM GDP, 0.1% fat free BSA and 0.2 nM GTP [γ-$^{35}$S] (1200 Ci/mmol). After incubation in 96 well microtiterplates at RT for 120 min, unbound GTP [γ-$^{35}$S] is separated by a centrifugation step. Luminescence of SPA beads triggered by membrane bound GTP [γ-$^{35}$S] is quantified with a TOPcount plate reader (Packard). EC$_{50}$s are calculated using standard curve fitting software. For example, the following results are obtained:

| Ex. | S1P$_1$ EC$_{50}$ [nM] | | S1P$_2$ EC$_{50}$ [nM] | | S1P$_3$ EC$_{50}$ [nM] | | S1P$_4$ EC$_{50}$ [nM] | | S1P$_5$ EC$_{50}$ [nM] | |
|---|---|---|---|---|---|---|---|---|---|---|
| 34 | 16.1 | Agon | >10000 | — | >10000 | — | 15.3 | Agon | 0.9 | Agon |
| 42 | 4.1 | Agon | >10000 | — | >10000 | — | 1.8 | Agon | 21.7 | Agon |
| 49 | 0.2 | Agon | >10000 | — | 47 | Agon | >10000 | — | 10 | Agon |
| 50 | 0.3 | Agon | >10000 | — | 196 | Agon | >10000 | — | 1.5 | Agon |
| 87 | 23.6 | Agon | >10000 | — | >10000 | — | >10000 | — | 22 | Agon |
| 88 | 2.5 | Agon | >10000 | — | 97.6 | Agon | >10000 | — | 40 | Agon |
| 94 | 12.2 | Agon | >10000 | — | >10000 | — | n.d. | — | 4.9 | Agon |

Agon = agonist

B. In Vivo: Blood Lymphocyte Depletion

A compound of formula I or the vehicle is administered orally by gavage to rats. Tall blood for hematological monitoring is obtained on day −1 to give the baseline individual values, and at 2, 6, 24, 48 and 72 hours after application. In this assay, the compounds of formula I deplete peripheral blood lymphocytes when administered at a dose of 0.03 to 3 mg/kg.

For example, following results are obtained: depletion of peripheral blood lymphocytes by more than 50%

Example 1: 0.2 mg/kg p.o. after 6 h, 0.1 mg/kg p.o. after 24 h

Example 6: 0.06 mg/kg p.o. after 6 h, 0.05 mg/kg p.o. after 24 h

Example 14: 0.03 mg/kg p.o. after 6 h, 0.04 mg/kg p.o. after 24 h

Example 27: 0.1 mg/kg p.o. after 6 h, 0.03 mg/kg p.o. after 24 h

Example 31: 0.05 mg/kg p.o. after 6 h, 0.1 mg/kg p.o. after 48 h

Example 72: 0.07 mg/kg p.o. after 6 h, 0.03 mg/kg p.o. after 48 h

The compounds of formula I are, therefore, useful in the treatment and/or prevention of diseases or disorders mediated by lymphocytes interactions, e.g. in transplantation, such as acute or chronic rejection of cell, tissue or organ allo- or xenografts or delayed graft function, graft versus host disease, autoimmune diseases, e.g. rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, psoriasis, Graves ophthalmopathy, alopecia areata and others, allergic diseases, e.g. allergic asthma, atopic dermatitis, allergic rhinitis/conjunctivitis, allergic contact dermatitis, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, myocarditis or hepatitis, ischemia/reperfusion injury, e.g. myocardial infarction, stroke, gut ischemia, renal failure or hemorrhage shock, traumatic shock, cancer, e.g. breast cancer, T cell lymphomas or T cell leukemias, infectious diseases, e.g. toxic shock (e.g. superantigen induced), septic shock, adult respiratory distress syndrome or viral infections, e.g. AIDS, viral hepatitis, chronic bacterial infection, or senile dementia. Examples of cell, tissue or solid organ transplants include e.g. pancreatic islets, stem cells, bone marrow, corneal tissue, neuronal tissue, heart, lung, combined heart-lung, kidney, liver, bowel, pancreas, trachea or oesophagus. For the above uses the required dosage will of course vary depending on the mode of administration, the particular condition to be treated and the effect desired.

In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, for example, in divided doses up to four times a day or in retard form. Suitable unit dosage forms for oral administration comprise from ca. 0.1 to 50 mg active ingredient.

The compounds of formula I may be administered by any conventional route, in particular enterally, e.g. orally, e.g. in the form of tablets or capsules, or parenterally, e.g. in the form of injectable solutions or suspensions, topically, e.g. in the form of lotions, gels, ointments or creams, or in a nasal or a suppository form. Pharmaceutical compositions comprising a compound of formula I in free form or in pharmaceutically acceptable salt form in association with at least one pharmaceutical acceptable carrier or diluent may be manufactured in conventional manner by mixing with a pharmaceutically acceptable carrier or diluent.

The compounds of formula I may be administered in free form or in pharmaceutically acceptable salt form e.g. as indicated above. Such salts may be prepared in conventional manner and exhibit the same order of activity as the free compounds.

In accordance with the foregoing the present invention further provides:

1.1 A method for preventing or treating disorders or diseases mediated by lymphocytes, e.g. such as indicated above, in a subject in need of such treatment, which method comprises administering to said subject an effective amount of a compound of formula I or a pharmaceutically acceptable salt thereof;

1.2 A method for preventing or treating acute or chronic transplant rejection or T-cell mediated inflammatory or autoimmune diseases, e.g. as indicated above, in a subject in need of such treatment, which method comprises administering to said subject an effective amount of a compound of formula I or a pharmaceutically acceptable salt thereof;

2. A compound of formula I, in free form or in a pharmaceutically acceptable salt form for use as a pharmaceutical, e.g. in any of the methods as indicated under 1.1 or 1.2 above.

3. A pharmaceutical composition, e.g. for use in any of the methods as in 1.1 or 1.2 above comprising a compound of formula I in free form or pharmaceutically acceptable salt form in association with a pharmaceutically acceptable diluent or carrier therefor.

4. A compound of formula I or a pharmaceutically acceptable salt thereof for use in the preparation of a pharmaceutical composition for use in any of the method as in 1.1 or 1.2 above.

The compounds of formula I may be administered as the sole active ingredient or in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders, or a chemotherapeutic agent, e.g a malignant cell anti-proliferative agent. For example, the compounds of formula I may be used in combination with a calcineurin inhibitor, e.g. cyclosporin A or FK 506; a mTOR inhibitor, e.g. rapamycin, 40-O-(2-hydroxyethyl)-rapamycin, CC1779, ABT578 or AP23573; an ascomycin having immuno-suppressive properties, e.g. ABT-281, ASM981, etc.; corticosteroids; cyclophosphamide; azathioprene; methotrexate; leflunomide; mizoribine; mycophenolic acid; mycophenolate mofetil; 15-deoxyspergualine or an immunosuppressive homologue, analogue or derivative thereof; immunosuppressive monoclonal antibodies, e.g., monoclonal antibodies to leukocyte receptors, e.g., MHC, CD2, CD3, CD4, CD7, CD8, CD25, CD28, CD40. CD45, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. L-A29Y; adhesion molecule inhibitors, e.g. LFA-1 antagonists, ICAM-1 or -3 antagonists, VCAM-4 antagonists or VLA-4 antagonists; or a chemotherapeutic agent, e.g. paclitaxel, gemcitabine, cisplatinum, doxorubicin or 5-fluorouracil; or an anti-infectious agent.

Where the compounds of formula I are administered in conjunction with other immunosuppressive/immunomodulatory, anti-inflammatory chemotherapeutic or anti-infectious therapy, dosages of the co-administered immunosuppressant, immunomodulatory, anti-inflammatory, chemotherapeutic or anti-infectious compound will of course vary depending on the type of co-drug employed, e.g. whether it is a steroid or a calcineurin inhibitor, on the specific drug employed, on the condition being treated and so forth. In accordance with the foregoing the present invention provides in a yet further aspect:

5. A method as defined above comprising co-administration, e.g. concomitantly or in sequence, of a therapeutically effective non-toxic amount of a compound of formula I and at least a second drug substance, e.g. an immunosuppressant, immunomodulatory, anti-inflammatory or chemotherapeutic drug, e.g. as indicated above.

6. A pharmaceutical combination, e.g. a kit, comprising a) a first agent which is a compound of formula I as disclosed herein, in free form or in pharmaceutically acceptable salt form, and b) at least one co-agent, e.g. an immunosuppressant, immunomodulatory, anti-inflammatory, chemotherapeutic or anti-infectious agent. The kit may comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula I and a co-agent, are both administered to a patient simultaneously in the form of a single entity or dosage. The term "non-fixed combination" means that the active ingredients, e.g. a compound of formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

The invention claimed is:

1. A compound of formula I*:

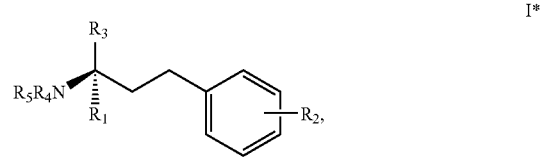

wherein $R_1$ is methyl;

$R_2$ is a residue of formula (c): —Y'—$(CH_2)_n$—$(CF_2)_m$—$CH_pF_q$(c), where Y' is a direct bond, O, CO, CHOH or C=$NOR_6$, wherein $R_6$ is H, $C_{1-4}$-alkyl, $C_{2-4}$-alkenyl, $C_{2-4}$-alkynyl or benzyl;

n is 0, 1, 2, 3, 4 or 5;

m is 0, 1, 2, 3, 4, 5 or 6, provided that the sum of n+m is 3-8;

each of p and q, independently, is 0, 1, 2 or 3, with the proviso that p+q=3;

and the chain $(CH_2)_n$—$(CF_2)_m$—$CH_pF_q$ contains at least two fluorine atoms and may, optionally, be interrupted by one carbon-carbon double or triple bond, one CO or one-to-three oxygen atoms;

$R_3$ is Z-$X_2$, where Z is $CH_2$, CHF, $CF_2$ or CHMe, and $X_2$ is OH or a residue of formula (a):

wherein $Z_1$ is a direct bond, $CH_2$, CHF, $CF_2$ or O, and each of $R_{12}$ and $R_{13}$, independently, is H or $C_{1-4}$-alkyl, optionally substituted by 1, 2 or 3 halogen atoms; and each of $R_4$ and $R_5$, independently, is H, $C_{1-4}$-alkyl optionally substituted by 1, 2 or 3 halogen atoms, or acyl;

in free form or in salt form.

2. A compound according to claim 1, where $R_2$ is selected from the group consisting of —Y—$C_nF_{2n+1}$, wherein n=3-8 and Y is $CH_2$, O or C=O;

—Y—$CH_2C_nF_{2n+1}$, wherein n=1-7 and Y is $CH_2$, O or C=O;

—Y—$CH_2CH_2C_nF_{2n+1}$, wherein n=1-6 and Y is $CH_2$, O or C=O;

—Y—$CH_2CH_2CH_2C_nF_{2n+1}$, wherein n=1-5 and Y is $CH_2$, O or C=O;

—Y—$(CH_2)_nCF_3$, wherein n=1-6 and Y is $CH_2$, O or C=O;

—Y—$(CH_2)_nCF_2CH_3$, wherein n=1-4 and Y is $CH_2$, O or C=O;

—Y—$(CH_2)_n(CF_2)_mCHF_2$, wherein n=0-3, m=1-6, n+m=3-7 and Y is $CH_2$, O or C=O; and —Y—$(CH_2)_nC(O)CF_3$, wherein n=1-5 and Y is $CH_2$, O or C=O.

3. A pharmaceutical composition comprising a compound according to claim 1, or a pharmaceutically-acceptable salt thereof in association with a pharmaceutically-acceptable diluent or carrier therefor.

4. A pharmaceutical combination comprising a compound according to claim 1, in free form or in pharmaceutically-acceptable salt form, and at least one co-agent selected from an immunosuppressant agent, an immunomodulatory agent, an anti-inflammatory agent and a chemotherapeutic drug.

5. A method for treating disorders or diseases mediated by lymphocytes, and for treating acute or chronic transplant rejection or T-cell-mediated inflammatory or autoimmune diseases in a subject comprising administering to the subject in need thereof an effective amount of a compound according to claim 1, or a pharmaceutically-acceptable salt thereof.

6. The compound according to claim 1 selected from the group consisting of:
- (R)-2-amino-2-methyl-4-[4-(4,4,5,5,5-pentafluoro-pentyloxy)-phenyl]-butan-1-ol hydrochloride;
- (R)-2-amino-2-methyl-4-[4-(6,6,6-trifluoro-hexyloxy)-phenyl]-butan-1-ol hydrochloride;
- 1-[4-((R)-3-amino-4-hydroxy-3-methyl-butyl)-phenyl]-6,6,6-trifluoro-hexan-1-one; and
- (R)-2-amino-2-methyl-4-[4-(7,7,7-trifluoro-heptyl)-phenyl]-butan-1-ol.

* * * * *

UNITED STATES PATENT AND TRADEMARK OFFICE
CERTIFICATE OF CORRECTION

| | |
|---|---|
| PATENT NO. | : 7,612,238 B2 |
| APPLICATION NO. | : 10/526760 |
| DATED | : November 3, 2009 |
| INVENTOR(S) | : Buehlmayer et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 234 days.

Signed and Sealed this

Nineteenth Day of October, 2010

David J. Kappos
*Director of the United States Patent and Trademark Office*